(12) United States Patent
Romey et al.

(10) Patent No.: US 8,715,589 B2
(45) Date of Patent: May 6, 2014

(54) SENSORS WITH THROMBORESISTANT COATING

(71) Applicant: Glumetrics, Inc., Irvine, CA (US)

(72) Inventors: Matthew A. Romey, Newport Beach, CA (US); Soya Gamsey, Huntington Beach, CA (US); David R. Markle, Berwyn, PA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 13/894,228

(22) Filed: May 14, 2013

(65) Prior Publication Data

US 2013/0267801 A1    Oct. 10, 2013

Related U.S. Application Data

(62) Division of application No. 12/895,394, filed on Sep. 30, 2010.

(60) Provisional application No. 61/247,500, filed on Sep. 30, 2009.

(51) Int. Cl.
*G01N 31/22* (2006.01)

(52) U.S. Cl.
USPC .......................................... 422/403; 600/316

(58) Field of Classification Search
USPC .......................................... 422/403; 600/316
See application file for complete search history.

(56) References Cited

U.S. PATENT DOCUMENTS

| | | | |
|---|---|---|---|
| 1,120,700 A | 12/1914 | Ehrlich |
| 1,334,901 A | 3/1920 | Higdon |
| 2,018,792 A | 10/1935 | Kern |
| 2,094,224 A | 9/1937 | Tietz et al. |
| 2,112,244 A | 3/1938 | Jurist |
| 2,274,551 A | 2/1942 | Kenyon et al. |
| 2,496,151 A | 1/1950 | Dawson et al. |
| 2,812,524 A | 11/1957 | Pruitt |
| 3,011,293 A | 12/1961 | Rado |
| 3,302,219 A | 2/1967 | Harris |
| 3,488,098 A | 1/1970 | Sobczak |
| 3,659,586 A | 5/1972 | Johns et al. |

(Continued)

FOREIGN PATENT DOCUMENTS

| | | |
|---|---|---|
| CN | 85108331 | 6/1987 |
| CS | 7707425 | 2/1980 |

(Continued)

OTHER PUBLICATIONS

Agayn, V. I. and Dr. R. Walt (1993). "Fiber-optic sensor for continuous monitoring of fermentation pH." Biotechnology 72(6):6-9.

(Continued)

*Primary Examiner* — Monique Cole
(74) *Attorney, Agent, or Firm* — Knobbe Martens Olson & Bear, LLP

(57) ABSTRACT

Embodiments of the present invention relate to analyte sensors comprising a heparin coating, and methods of coating analyte sensors. The heparin can be stably associated with at least a portion of a porous membrane that covers a portion of the analyte sensors. The heparin can be photochemically linked to the coating through the formation of covalent bonds.

23 Claims, 8 Drawing Sheets

(56) References Cited

U.S. PATENT DOCUMENTS

| | | |
|---|---|---|
| 3,685,059 A | 8/1972 | Bokros et al. |
| 3,795,239 A | 3/1974 | Eberhard et al. |
| 3,827,089 A | 8/1974 | Grow |
| 3,846,353 A | 11/1974 | Grotta |
| 3,865,548 A | 2/1975 | Padawer |
| 3,874,010 A | 4/1975 | Geary |
| 3,884,225 A | 5/1975 | Witter |
| 3,895,403 A | 7/1975 | Davis |
| 3,905,888 A | 9/1975 | Mindt et al. |
| 3,909,504 A | 9/1975 | Browne |
| 3,924,281 A | 12/1975 | Gibbs |
| 3,930,580 A | 1/1976 | Bazell et al. |
| 3,996,345 A | 12/1976 | Ullman et al. |
| 4,003,707 A | 1/1977 | Lübbers et al. |
| 4,041,932 A | 8/1977 | Fostick |
| 4,094,578 A | 6/1978 | DiVita et al. |
| 4,118,485 A | 10/1978 | Eriksson et al. |
| 4,180,879 A | 1/1980 | Mann |
| 4,197,853 A | 4/1980 | Parker |
| 4,200,110 A | 4/1980 | Peterson et al. |
| 4,240,438 A | 12/1980 | Updike et al. |
| 4,245,645 A | 1/1981 | Arseneault et al. |
| 4,269,605 A | 5/1981 | Dean et al. |
| 4,306,562 A | 12/1981 | Osborne |
| 4,307,933 A | 12/1981 | Palmer et al. |
| 4,308,254 A | 12/1981 | Tayot et al. |
| 4,344,438 A | 8/1982 | Schultz |
| 4,345,606 A | 8/1982 | Littleford |
| 4,358,851 A | 11/1982 | Scifres et al. |
| 4,361,918 A | 12/1982 | Roisaeth |
| 4,371,374 A | 2/1983 | Cerami et al. |
| 4,459,712 A | 7/1984 | Pathan |
| 4,465,335 A | 8/1984 | Eppes |
| 4,469,357 A | 9/1984 | Martin |
| 4,474,431 A | 10/1984 | Bricheno |
| 4,476,870 A | 10/1984 | Peterson et al. |
| 4,490,867 A | 1/1985 | Gabrielsson |
| 4,495,293 A | 1/1985 | Shaffar |
| 4,502,169 A | 3/1985 | Persson |
| RE31,879 E | 5/1985 | Lubbers et al. |
| 4,528,616 A | 7/1985 | Koppensteiner |
| 4,548,907 A | 10/1985 | Seitz et al. |
| 4,557,900 A | 12/1985 | Heitzmann |
| 4,560,248 A | 12/1985 | Cramp et al. |
| 4,568,444 A | 2/1986 | Nakamura et al. |
| 4,579,641 A | 4/1986 | Shimomura et al. |
| 4,600,310 A | 7/1986 | Cramp et al. |
| 4,621,049 A | 11/1986 | Wang |
| 4,629,451 A | 12/1986 | Winters et al. |
| 4,636,144 A | 1/1987 | Abe et al. |
| 4,649,271 A | 3/1987 | Hök et al. |
| 4,650,472 A | 3/1987 | Bates |
| 4,654,031 A | 3/1987 | Lentz |
| 4,654,127 A | 3/1987 | Baker et al. |
| 4,654,327 A | 3/1987 | Teng |
| 4,659,817 A | 4/1987 | Gallop et al. |
| 4,675,925 A | 6/1987 | Littleton |
| 4,684,538 A | 8/1987 | Klemarczyk |
| 4,689,308 A | 8/1987 | Gerhard |
| RE32,514 E | 10/1987 | Steklenski |
| 4,703,756 A | 11/1987 | Gough et al. |
| 4,707,056 A | 11/1987 | Bittner |
| 4,710,623 A | 12/1987 | Lipson et al. |
| 4,727,730 A | 3/1988 | Boiarski et al. |
| 4,737,153 A | 4/1988 | Shimamura et al. |
| 4,744,618 A | 5/1988 | Mahlein |
| 4,746,751 A | 5/1988 | Oviatt, Jr. et al. |
| 4,750,795 A | 6/1988 | Blotekjaer |
| 4,751,918 A | 6/1988 | Bernard et al. |
| 4,754,538 A | 7/1988 | Stewart, Jr. et al. |
| 4,776,047 A | 10/1988 | DiMatteo |
| 4,785,814 A | 11/1988 | Kane |
| 4,792,689 A | 12/1988 | Peterson |
| 4,794,619 A | 12/1988 | Tregay |
| 4,796,633 A | 1/1989 | Zwirkoski |
| 4,798,738 A | 1/1989 | Yafuso et al. |
| 4,801,187 A | 1/1989 | Elbert et al. |
| 4,803,049 A | 2/1989 | Hirschfeld et al. |
| 4,810,655 A | 3/1989 | Khalil et al. |
| 4,816,130 A | 3/1989 | Karakelle et al. |
| 4,820,636 A | 4/1989 | Hill et al. |
| 4,821,738 A | 4/1989 | Iwasaki et al. |
| 4,822,127 A | 4/1989 | Kamiya et al. |
| 4,833,091 A | 5/1989 | Leader et al. |
| 4,838,269 A | 6/1989 | Robinson et al. |
| 4,844,841 A | 7/1989 | Koller et al. |
| 4,846,543 A | 7/1989 | Kapany et al. |
| 4,851,195 A | 7/1989 | Matthews et al. |
| 4,854,321 A | 8/1989 | Boiarski |
| 4,861,728 A | 8/1989 | Wagner |
| 4,872,226 A | 10/1989 | Lonardo |
| 4,872,759 A | 10/1989 | Stich-Baumeister et al. |
| 4,886,338 A | 12/1989 | Yafuso et al. |
| 4,889,407 A | 12/1989 | Markle et al. |
| 4,903,707 A | 2/1990 | Knute et al. |
| 4,906,232 A | 3/1990 | Reynolds |
| 4,923,273 A | 5/1990 | Taylor |
| 4,927,222 A | 5/1990 | Kamiya et al. |
| 4,937,901 A | 7/1990 | Brennan |
| 4,939,801 A | 7/1990 | Schaal et al. |
| 4,941,308 A | 7/1990 | Grabenkort et al. |
| 4,943,364 A | 7/1990 | Koch et al. |
| 4,946,038 A | 8/1990 | Eaton |
| 4,955,862 A | 9/1990 | Sepetka |
| 4,960,412 A | 10/1990 | Fink |
| 4,966,597 A | 10/1990 | Cosman |
| 5,000,901 A | 3/1991 | Iyer et al. |
| 5,005,576 A | 4/1991 | Gunther |
| 5,007,704 A | 4/1991 | McCartney |
| 5,012,809 A | 5/1991 | Shulze |
| 5,018,225 A | 5/1991 | Fergni et al. |
| 5,030,420 A | 7/1991 | Bacon et al. |
| 5,047,020 A | 9/1991 | Hsu |
| 5,047,208 A | 9/1991 | Schweitzer et al. |
| 5,047,627 A | 9/1991 | Yim et al. |
| 5,054,497 A | 10/1991 | Kapp et al. |
| 5,068,931 A | 12/1991 | Smith |
| 5,069,674 A | 12/1991 | Fearnot et al. |
| 5,082,112 A | 1/1992 | Dunklee |
| 5,093,266 A | 3/1992 | Leader et al. |
| 5,098,618 A | 3/1992 | Zelez |
| 5,104,388 A | 4/1992 | Quackenbush |
| 5,108,502 A | 4/1992 | Pawlowski et al. |
| 5,109,452 A | 4/1992 | Selvin et al. |
| 5,114,676 A | 5/1992 | Leiner et al. |
| 5,119,463 A | 6/1992 | Vurek et al. |
| 5,132,432 A | 7/1992 | Haugland et al. |
| 5,137,033 A | 8/1992 | Norton |
| 5,137,833 A | 8/1992 | Russell |
| 5,141,497 A | 8/1992 | Erskine |
| 5,156,962 A | 10/1992 | Suzuki et al. |
| 5,162,130 A | 11/1992 | McLaughlin |
| 5,166,990 A | 11/1992 | Riccitelli et al. |
| 5,167,715 A | 12/1992 | Kalafala et al. |
| 5,168,587 A | 12/1992 | Shutes |
| 5,175,016 A | 12/1992 | Yafuso et al. |
| 5,176,882 A | 1/1993 | Gray et al. |
| 5,178,267 A | 1/1993 | Grabenkort et al. |
| 5,180,376 A | 1/1993 | Fischell |
| 5,182,353 A | 1/1993 | Hui et al. |
| 5,185,263 A | 2/1993 | Kroneis et al. |
| 5,188,803 A | 2/1993 | Hochberg |
| 5,217,691 A | 6/1993 | Greene et al. |
| 5,230,031 A | 7/1993 | Markle |
| 5,246,109 A | 9/1993 | Markle et al. |
| 5,246,441 A | 9/1993 | Ross et al. |
| 5,257,338 A | 10/1993 | Markle |
| 5,262,037 A | 11/1993 | Markle et al. |
| 5,279,596 A | 1/1994 | Castaneda et al. |
| 5,280,130 A | 1/1994 | Markle et al. |
| 5,280,548 A | 1/1994 | Atwater et al. |
| 5,284,154 A | 2/1994 | Raymond et al. |
| 5,286,294 A | 2/1994 | Ebi et al. |
| 5,290,266 A | 3/1994 | Rohling et al. |

(56) References Cited

U.S. PATENT DOCUMENTS

| | | | |
|---|---|---|---|
| 5,302,731 | A | 4/1994 | Pitner et al. |
| 5,305,740 | A | 4/1994 | Kolobow |
| 5,310,471 | A | 5/1994 | Markle et al. |
| 5,312,344 | A | 5/1994 | Grinfeld |
| 5,322,513 | A | 6/1994 | Walker |
| 5,330,718 | A | 7/1994 | Hui et al. |
| 5,334,157 | A | 8/1994 | Klein et al. |
| 5,335,305 | A | 8/1994 | Kosa et al. |
| 5,354,448 | A | 10/1994 | Markle et al. |
| 5,357,732 | A | 10/1994 | Markle et al. |
| 5,361,758 | A | 11/1994 | Hall et al. |
| 5,380,304 | A | 1/1995 | Parker |
| 5,389,217 | A | 2/1995 | Singer |
| 5,408,999 | A | 4/1995 | Singh et al. |
| 5,409,469 | A | 4/1995 | Schaerf |
| 5,503,770 | A | 4/1996 | James et al. |
| 5,511,408 | A | 4/1996 | Yoshioka et al. |
| 5,511,547 | A | 4/1996 | Markle et al. |
| 5,512,246 | A | 4/1996 | Russell et al. |
| 5,514,710 | A | 5/1996 | Haugland et al. |
| 5,536,783 | A | 7/1996 | Olstein et al. |
| 5,545,179 | A | 8/1996 | Williamson, IV |
| 5,558,714 | A | 9/1996 | Watanabe et al. |
| 5,569,186 | A | 10/1996 | Lord et al. |
| 5,596,988 | A | 1/1997 | Markle et al. |
| 5,605,152 | A | 2/1997 | Slate et al. |
| 5,618,587 | A | 4/1997 | Markle et al. |
| 5,622,259 | A | 4/1997 | Church |
| 5,634,911 | A | 6/1997 | Hermann et al. |
| 5,643,212 | A | 7/1997 | Coutre et al. |
| 5,643,580 | A | 7/1997 | Subramaniam |
| 5,658,264 | A | 8/1997 | Samson |
| 5,669,920 | A | 9/1997 | Conley et al. |
| 5,676,784 | A | 10/1997 | McGaffigan |
| D388,418 | S | 12/1997 | Polson et al. |
| 5,700,253 | A | 12/1997 | Parker |
| 5,702,373 | A | 12/1997 | Samson |
| 5,747,666 | A | 5/1998 | Willis |
| 5,755,704 | A | 5/1998 | Lunn |
| 5,763,238 | A | 6/1998 | James et al. |
| 5,797,876 | A | 8/1998 | Spears et al. |
| 5,810,985 | A | 9/1998 | Bao et al. |
| 5,827,242 | A | 10/1998 | Follmer et al. |
| 5,891,100 | A | 4/1999 | Fleckenstein |
| 5,891,114 | A | 4/1999 | Chien et al. |
| 5,922,612 | A | 7/1999 | Alder et al. |
| 5,947,940 | A | 9/1999 | Beisel |
| 5,951,929 | A | 9/1999 | Wilson |
| 5,954,651 | A | 9/1999 | Berg et al. |
| 6,002,954 | A | 12/1999 | Van Antwerp et al. |
| 6,011,984 | A | 1/2000 | Van Antwerp et al. |
| 6,019,736 | A | 2/2000 | Avellanet et al. |
| 6,117,290 | A | 9/2000 | Say et al. |
| 6,152,933 | A | 11/2000 | Werp et al. |
| 6,156,010 | A | 12/2000 | Kuracina et al. |
| 6,175,752 | B1 | 1/2001 | Say et al. |
| 6,187,130 | B1 | 2/2001 | Berard et al. |
| 6,197,534 | B1 | 3/2001 | Lakowicz et al. |
| 6,200,301 | B1 | 3/2001 | Pfeiffer et al. |
| 6,227,627 | B1 | 5/2001 | Goossens |
| 6,254,829 | B1 | 7/2001 | Hartmann et al. |
| 6,273,874 | B1 | 8/2001 | Parris |
| 6,304,766 | B1 | 10/2001 | Colvin, Jr. |
| 6,319,540 | B1 | 11/2001 | Van Antwerp et al. |
| 6,361,508 | B1 | 3/2002 | Johnson et al. |
| 6,363,273 | B1 | 3/2002 | Mastrorio et al. |
| 6,370,406 | B1 | 4/2002 | Wach et al. |
| 6,375,627 | B1 | 4/2002 | Mauze et al. |
| 6,387,672 | B1 | 5/2002 | Arimori et al. |
| 6,464,849 | B1 | 10/2002 | Say et al. |
| 6,477,395 | B2 | 11/2002 | Shulman et al. |
| 6,521,447 | B2 | 2/2003 | Zou et al. |
| 6,544,212 | B2 | 4/2003 | Galley et al. |
| 6,584,335 | B1 | 6/2003 | Haar et al. |
| 6,585,665 | B1 | 7/2003 | Chapman et al. |
| 6,602,702 | B1 | 8/2003 | Anslyn et al. |
| 6,623,490 | B1 | 9/2003 | Crane et al. |
| 6,627,177 | B2 | 9/2003 | Singaram et al. |
| 6,653,141 | B2 | 11/2003 | Singaram et al. |
| 6,663,595 | B2 | 12/2003 | Spohn et al. |
| 6,682,938 | B1 | 1/2004 | Satcher, Jr. et al. |
| 6,702,972 | B1 | 3/2004 | Markle |
| 6,711,423 | B2 | 3/2004 | Colvin |
| 6,741,877 | B1 | 5/2004 | Shults et al. |
| 6,766,183 | B2 | 7/2004 | Walsh et al. |
| 6,794,195 | B2 | 9/2004 | Colvin, Jr. |
| 6,800,451 | B2 | 10/2004 | Daniloff et al. |
| 6,804,544 | B2 | 10/2004 | Van Antwerp et al. |
| 6,855,556 | B2 | 2/2005 | Amiss et al. |
| 6,858,403 | B2 | 2/2005 | Han et al. |
| 7,033,322 | B2 * | 4/2006 | Silver ............................ 600/486 |
| 7,064,103 | B2 | 6/2006 | Pitner et al. |
| D525,632 | S | 7/2006 | Jost et al. |
| RE39,438 | E | 12/2006 | Shah et al. |
| 7,181,260 | B2 | 2/2007 | Gutierrez |
| 7,216,001 | B2 | 5/2007 | Hacker et al. |
| D544,871 | S | 6/2007 | Lim et al. |
| 7,226,414 | B2 | 6/2007 | Ballerstadt et al. |
| 7,229,450 | B1 | 6/2007 | Chitre et al. |
| D550,242 | S | 9/2007 | Niijima |
| D550,245 | S | 9/2007 | Niijima |
| 7,276,029 | B2 | 10/2007 | Goode, Jr. et al. |
| 7,277,740 | B2 | 10/2007 | Rohleder et al. |
| 7,277,745 | B2 | 10/2007 | Natarajan et al. |
| 7,303,814 | B2 | 12/2007 | Lamberti et al. |
| 7,306,621 | B1 | 12/2007 | Halla et al. |
| D559,264 | S | 1/2008 | Niijima |
| D560,224 | S | 1/2008 | Park et al. |
| 7,316,909 | B2 | 1/2008 | Pitner et al. |
| 7,317,111 | B2 | 1/2008 | Bhatt et al. |
| 7,326,538 | B2 | 2/2008 | Pitner et al. |
| 7,345,160 | B2 | 3/2008 | Daunert et al. |
| 7,353,055 | B2 | 4/2008 | Hogan |
| 7,358,094 | B2 | 4/2008 | Bell et al. |
| 7,381,184 | B2 | 6/2008 | Funderburk et al. |
| 7,381,938 | B2 | 6/2008 | Kobayashi et al. |
| 7,390,462 | B2 | 6/2008 | Rao et al. |
| 7,417,164 | B2 | 8/2008 | Suri |
| D580,950 | S | 11/2008 | Steele et al. |
| D582,939 | S | 12/2008 | Neuhaus |
| 7,470,420 | B2 | 12/2008 | Singaram et al. |
| 7,496,392 | B2 | 2/2009 | Alarcon et al. |
| D592,223 | S | 5/2009 | Neuhaus |
| 7,559,894 | B2 | 7/2009 | McEowen |
| 7,615,007 | B2 | 11/2009 | Shults et al. |
| D610,065 | S | 2/2010 | Gallert |
| 7,661,301 | B2 | 2/2010 | Moor |
| 7,751,863 | B2 | 7/2010 | Markle et al. |
| 7,767,846 | B2 | 8/2010 | Suri |
| D626,143 | S | 10/2010 | Karten et al. |
| 7,807,210 | B1 | 10/2010 | Roorda et al. |
| 7,824,918 | B2 | 11/2010 | Suri |
| 7,829,341 | B2 | 11/2010 | Gamsey et al. |
| 7,879,024 | B2 | 2/2011 | Thorstenson et al. |
| 7,881,780 | B2 | 2/2011 | Flaherty |
| 7,939,664 | B2 | 5/2011 | Gamsey et al. |
| 7,959,577 | B2 | 6/2011 | Schmitz et al. |
| 7,981,058 | B2 | 7/2011 | Akay |
| 8,088,097 | B2 | 1/2012 | Markle et al. |
| 8,110,251 | B2 | 2/2012 | Markle et al. |
| 8,178,676 | B2 | 5/2012 | Gamsey et al. |
| 8,202,731 | B2 | 6/2012 | Suri |
| 8,467,843 | B2 | 6/2013 | Markle et al. |
| 8,473,222 | B2 | 6/2013 | Romey et al. |
| 8,512,245 | B2 | 8/2013 | Markle et al. |
| 8,535,262 | B2 | 9/2013 | Markle et al. |
| 2001/0016682 | A1 | 8/2001 | Berner et al. |
| 2002/0018843 | A1 | 2/2002 | Van Antwerp et al. |
| 2002/0026108 | A1 | 2/2002 | Colvin, Jr. |
| 2002/0107178 | A1 | 8/2002 | Van Den Berghe |
| 2002/0128546 | A1 | 9/2002 | Silver |
| 2002/0193672 | A1 | 12/2002 | Walsh et al. |
| 2003/0013974 | A1 | 1/2003 | Natarajan et al. |
| 2003/0028089 | A1 | 2/2003 | Galley et al. |

(56) References Cited

U.S. PATENT DOCUMENTS

| | | |
|---|---|---|
| 2003/0065254 A1 | 4/2003 | Schulman et al. |
| 2003/0100821 A1 | 5/2003 | Heller et al. |
| 2003/0171666 A1 | 9/2003 | Loeb et al. |
| 2003/0232198 A1 | 12/2003 | Lamberti et al. |
| 2003/0232383 A1 | 12/2003 | Daunert et al. |
| 2004/0028612 A1 | 2/2004 | Singaram et al. |
| 2004/0072358 A1 | 4/2004 | Ballerstadt |
| 2004/0077969 A1 | 4/2004 | Onda et al. |
| 2004/0087842 A1 | 5/2004 | Lakowicz et al. |
| 2004/0136924 A1 | 7/2004 | Boyd et al. |
| 2004/0176672 A1 | 9/2004 | Silver et al. |
| 2004/0219535 A1 | 11/2004 | Bell et al. |
| 2004/0230138 A1 | 11/2004 | Inoue et al. |
| 2004/0243018 A1 | 12/2004 | Organ et al. |
| 2004/0260158 A1 | 12/2004 | Hogan |
| 2004/0260162 A1 | 12/2004 | Rohleder et al. |
| 2004/0267203 A1 | 12/2004 | Potter et al. |
| 2005/0019219 A1 | 1/2005 | Oshiman et al. |
| 2005/0048121 A1 | 3/2005 | East et al. |
| 2005/0054975 A1 | 3/2005 | Patel et al. |
| 2005/0059097 A1 | 3/2005 | Daunert et al. |
| 2005/0090014 A1 | 4/2005 | Rao et al. |
| 2005/0113658 A1 | 5/2005 | Jacobson et al. |
| 2005/0118599 A1 | 6/2005 | Pawliszyn |
| 2005/0118726 A1 | 6/2005 | Schultz et al. |
| 2005/0123935 A1 | 6/2005 | Haugland et al. |
| 2005/0124896 A1 | 6/2005 | Richter et al. |
| 2005/0130249 A1 | 6/2005 | Parris et al. |
| 2005/0173245 A1 | 8/2005 | Feldman et al. |
| 2005/0193860 A1 | 9/2005 | Schulman et al. |
| 2005/0233465 A1 | 10/2005 | Miller |
| 2005/0240086 A1 | 10/2005 | Akay |
| 2005/0241959 A1 | 11/2005 | Ward et al. |
| 2005/0266038 A1 | 12/2005 | Glauser et al. |
| 2005/0267326 A1 | 12/2005 | Loeb et al. |
| 2005/0282225 A1 | 12/2005 | Daunert et al. |
| 2005/0283204 A1 | 12/2005 | Buhlmann et al. |
| 2006/0008500 A1 | 1/2006 | Chavan et al. |
| 2006/0039950 A1 | 2/2006 | Zhou et al. |
| 2006/0051874 A1 | 3/2006 | Reed et al. |
| 2006/0079740 A1 | 4/2006 | Silver et al. |
| 2006/0083688 A1 | 4/2006 | Singaram et al. |
| 2006/0084854 A1 | 4/2006 | Cho et al. |
| 2006/0088722 A1 | 4/2006 | Aller et al. |
| 2006/0105174 A1 | 5/2006 | Aller et al. |
| 2006/0135888 A1 | 6/2006 | Mimnagh-Kelleher et al. |
| 2006/0173252 A1 | 8/2006 | Ellingsen et al. |
| 2006/0189863 A1 | 8/2006 | Peyser et al. |
| 2006/0189979 A1 | 8/2006 | Esch et al. |
| 2006/0195042 A1 | 8/2006 | Flaherty |
| 2006/0270949 A1 | 11/2006 | Mathie et al. |
| 2006/0287600 A1 | 12/2006 | McEowen |
| 2007/0003588 A1 | 1/2007 | Chinn et al. |
| 2007/0014726 A1 | 1/2007 | Merical et al. |
| 2007/0020181 A1 | 1/2007 | Workman et al. |
| 2007/0038155 A1 | 2/2007 | Kelly et al. |
| 2007/0060872 A1 | 3/2007 | Hall et al. |
| 2007/0100356 A1 | 5/2007 | Lucatero et al. |
| 2007/0123775 A1 | 5/2007 | Meyer et al. |
| 2007/0136825 A1 | 6/2007 | Frommer et al. |
| 2007/0156079 A1 | 7/2007 | Brown |
| 2007/0175828 A1 | 8/2007 | Goedje et al. |
| 2007/0179437 A1 | 8/2007 | Grage et al. |
| 2007/0207498 A1 | 9/2007 | Palmieri et al. |
| 2007/0244382 A1 | 10/2007 | Robinson et al. |
| 2007/0256477 A1 | 11/2007 | Moor |
| 2007/0265675 A1 | 11/2007 | Lund et al. |
| 2008/0001091 A1 | 1/2008 | Kobayashi et al. |
| 2008/0009687 A1 | 1/2008 | Smith et al. |
| 2008/0027245 A1 | 1/2008 | Suri |
| 2008/0086042 A1 | 4/2008 | Brister et al. |
| 2008/0154101 A1 | 6/2008 | Jain et al. |
| 2008/0154107 A1 | 6/2008 | Jina |
| 2008/0183061 A1 | 7/2008 | Goode et al. |
| 2008/0187655 A1* | 8/2008 | Markle et al. .................. 427/154 |
| 2008/0188722 A1 | 8/2008 | Markle et al. |
| 2008/0188725 A1 | 8/2008 | Markle et al. |
| 2008/0261255 A1 | 10/2008 | Tolosa et al. |
| 2008/0287761 A1 | 11/2008 | Hayter et al. |
| 2008/0305009 A1 | 12/2008 | Gamsey et al. |
| 2008/0305506 A1 | 12/2008 | Suri |
| 2008/0306363 A1 | 12/2008 | Chaiken et al. |
| 2008/0311675 A1 | 12/2008 | Thomas et al. |
| 2008/0312560 A1 | 12/2008 | Jamsen et al. |
| 2009/0005266 A1 | 1/2009 | Ostermeier et al. |
| 2009/0018418 A1 | 1/2009 | Markle et al. |
| 2009/0018426 A1 | 1/2009 | Markle et al. |
| 2009/0048430 A1 | 2/2009 | Hellinga et al. |
| 2009/0061528 A1 | 3/2009 | Suri |
| 2009/0062696 A1 | 3/2009 | Nathan et al. |
| 2009/0076336 A1 | 3/2009 | Mazar et al. |
| 2009/0081803 A1 | 3/2009 | Gamsey et al. |
| 2009/0082566 A1 | 3/2009 | Mitra |
| 2009/0088329 A1 | 4/2009 | Brennan et al. |
| 2009/0104714 A1 | 4/2009 | Thomas et al. |
| 2009/0112075 A1 | 4/2009 | Klok et al. |
| 2009/0143659 A1 | 6/2009 | Li et al. |
| 2009/0171381 A1 | 7/2009 | Schmitz et al. |
| 2009/0177143 A1 | 7/2009 | Markle et al. |
| 2009/0182217 A1 | 7/2009 | Li et al. |
| 2009/0192416 A1 | 7/2009 | Ernst et al. |
| 2009/0196864 A1 | 8/2009 | Bulla |
| 2009/0200620 A1 | 8/2009 | Omura et al. |
| 2009/0228068 A1 | 9/2009 | Buhlmann et al. |
| 2009/0264719 A1 | 10/2009 | Markle et al. |
| 2009/0324945 A1 | 12/2009 | Licht et al. |
| 2010/0173065 A1* | 7/2010 | Michal et al. .................. 427/2.21 |
| 2010/0274110 A1 | 10/2010 | Markle |
| 2010/0279424 A1 | 11/2010 | Suri |
| 2010/0292617 A1 | 11/2010 | Lei et al. |
| 2010/0312483 A1 | 12/2010 | Peysr |
| 2011/0077477 A1 | 3/2011 | Romey et al. |
| 2011/0105866 A1 | 5/2011 | Markle |
| 2011/0152658 A1 | 6/2011 | Peyser |
| 2011/0171742 A1 | 7/2011 | Gamsey |
| 2011/0224516 A1 | 9/2011 | Romey et al. |
| 2011/0236989 A1 | 9/2011 | Suri et al. |
| 2011/0263953 A1 | 10/2011 | Markle |
| 2012/0053427 A1 | 3/2012 | Markle et al. |
| 2012/0116191 A1 | 5/2012 | Markle et al. |
| 2012/0208286 A1 | 8/2012 | Gamsey et al. |
| 2012/0282412 A1 | 11/2012 | Markle et al. |
| 2013/0267802 A1 | 10/2013 | Markle |
| 2013/0287631 A1 | 10/2013 | Romey |

FOREIGN PATENT DOCUMENTS

| | | |
|---|---|---|
| DE | 3036868 | 5/1982 |
| DE | 3509262 | 10/1985 |
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 596 700 | 5/1994 |
| EP | 0 617 977 A1 | 10/1994 |
| EP | 0 758 451 B1 | 1/1999 |
| EP | 000760723-0001 | 7/2007 |
| EP | 2 217 316 | 7/2010 |
| EP | 2 222 686 | 8/2010 |
| EP | 2 147 003 | 4/2011 |
| EP | 2 054 476 | 6/2011 |
| FR | 2 350 831 | 12/1977 |
| FR | 2 624 007 | 6/1989 |
| GB | 1 123 094 | 8/1968 |
| GB | 1 447 163 | 8/1976 |
| GB | 2 048 682 | 12/1980 |
| JP | 53-68249 | 6/1978 |
| JP | 54-13347 | 1/1979 |
| JP | 54-111363 | 8/1979 |
| JP | 54-155856 | 12/1979 |

(56) References Cited

FOREIGN PATENT DOCUMENTS

| | | |
|---|---|---|
| JP | 56-116752 | 9/1981 |
| JP | 56-116754 | 9/1981 |
| JP | 58-162921 | 9/1983 |
| JP | 3-52936 | 3/1991 |
| JP | 06-016859 | 4/1994 |
| JP | 06-285049 | 10/1994 |
| JP | 2003-262613 | 9/2003 |
| JP | 1332866 | 5/2008 |
| JP | 2009-544729 | 12/2009 |
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| JP | 2 438 152 | 4/2012 |
| SU | 6216724 | 8/1978 |
| WO | WO 87/00920 | 2/1987 |
| WO | WO 88/04415 | 6/1988 |
| WO | WO 91/09312 | 6/1991 |
| WO | WO 92/19150 | 11/1992 |
| WO | WO 94/10553 | 5/1994 |
| WO | WO 95/30148 | 11/1995 |
| WO | WO 96/22730 | 8/1996 |
| WO | WO 96/22798 | 8/1996 |
| WO | WO 97/20530 | 6/1997 |
| WO | WO 97/37713 | 10/1997 |
| WO | WO 97/48437 | 12/1997 |
| WO | WO 98/08554 | 3/1998 |
| WO | WO 00/02048 | 1/2000 |
| WO | WO 00/13003 | 3/2000 |
| WO | WO 00/43536 | 7/2000 |
| WO | WO 01/20019 | 3/2001 |
| WO | WO 01/60248 | 8/2001 |
| WO | WO 02/046752 | 6/2002 |
| WO | WO 03/034047 | 4/2003 |
| WO | WO 03/060464 | 7/2003 |
| WO | WO 2004/054438 | 7/2004 |
| WO | WO 2004/099778 | 11/2004 |
| WO | WO 2005/090014 | 4/2005 |
| WO | WO 2005/054831 | 6/2005 |
| WO | WO 2005/065241 | 7/2005 |
| WO | WO 2006/023725 | 3/2006 |
| WO | WO 2006/044973 | 4/2006 |
| WO | WO 2007/059311 | 5/2007 |
| WO | WO 2007/067743 | 6/2007 |
| WO | WO 2007/105140 | 9/2007 |
| WO | WO 2008/001091 | 1/2008 |
| WO | WO 2008/014280 | 1/2008 |
| WO | WO 2008/072338 | 6/2008 |
| WO | WO 2008/097747 | 8/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |
| WO | WO 2010/123972 | 10/2010 |
| WO | WO 2010/141888 | 12/2010 |
| WO | WO 2011/041546 | 4/2011 |
| WO | WO 2011/056274 | 5/2011 |
| WO | WO 2011/075710 | 6/2011 |
| WO | WO 2011/075711 | 6/2011 |
| WO | WO 2011/084713 | 7/2011 |
| WO | WO 2011/097586 | 8/2011 |
| WO | WO 2011/112020 | 9/2011 |
| WO | WO 2011/137178 | 11/2011 |
| WO | WO 2013/033076 | 3/2013 |
| WO | WO 2013/049068 | 4/2013 |

OTHER PUBLICATIONS

Atherton, S. J., et al.: "Reactions of Three Bis(viologen) Tetraquaternary Salts and Their Reduced Radicals", J. Am. Chem. Soc. 1986, 108,3380-3385.

Badugu R., et al, "Wavelength-rationnetric near-physiological pH sensors based on 6-aminoquinolinium boronic acid probes" Talanta, Elsevier, Amsterdam, NL, Apr. 30, 2005, vol. 66, Issue No. 3, pp. 569-574.

Badugu, R. et al. "Boronic acid fluorescents ensors for monosaccharide signaling based on the 6-methoxyquinolinium heterocyclic nucleus: progress toward noninvasive and continuous glucose monitoring." 2005 Bioorg. Med. Chem. 13 (1):113-119.

Badugu, R. et al. "Fluorescence sensors for monosaccharides based on the 6-methylquinolinium nucleus and boronic acid moiety: potential application to ophthalmic diagnostics." 2005 Talanta 65 (3):762-768.

Benmakroha et al. "Haemocompatibility of invasive sensors," Med. & Biol. Eng. & Comput., 1995, 33,811-821 (Nov. 1995).

Cappuccio, F.E. et al. 2004 "Evaluation of pyranine derivatives in boronic acid based saccharide sensing: Significance of charge interaction between dye and quencher in solution and hydrogel" Journal of Fluorescence 14:521-533.

Cao, H., et al.: "Fluorescent Chemosensors for Carbohydrates: A Decade's Worth of Bright Spies for Saccharides in Review", Journal of Fluorescence, vol. 14, No. 5, Sep. 2004.

Cordes, D. B., et al., 2006, in Topics in Fluorescence Spectroscopy; vol. 11, Glucose Sensing, Springer "Two component optical sugar sensing using boronic acid-substituted viologens with anionic fluorescent dyes" pp. 47-87. (ISBN: 978-0-387-29571-8 p. 76, scheme 3.7).

Cordes, D. B., et al.: "The Interaction of Boronic Acid-Substituted Viologens with Pyranine: The Effects of Quencher Charge on Fluorescence Quenching and Glucose Response", Langmuir 2005,21, 6540-6547.

DiCesare, N., et al.: "Saccharide Detection Based on the Amplified Fluorescence Quenching of a Water-Soluble Poly(phenylene ethynylene) by a Boronic Acid Functionalized Benzyl Viologen Derivativ~", LanQrnuir.2002,18, 7785-7787.

EPO Exam Report re EP App. No. 08 728 399.0, dated Dec. 7, 2010.

European Examination Report dated May 11, 2010, re EP Application No. 08 729 209.0.

European Examination Report dated Jan. 25, 2012, re EP Application No. 08 729209.0.

EPO Office Action re App. No. 07 799 791.4 dated Jan. 29, 2010.

European Examination Report re Application No. 08 755 267.5, dated Apr. 26, 2010.

European Examination Report re Application No. 08 755 267.5, dated Sep. 14, 2010.

European Examination Report re App, No. 08 797 302.0, dated Nov. 7, 2011.

European Examination Report re App. No. 08 797 302.0, dated Jan. 24, 2011.

European Examination dated Apr. 1, 2010, re EP Application No. 08 769 266.1-1211.

Gamsey, S. et al. 2007 "Boronic acid based bipyridinium salts as tunable receptors for monosaccharides and alpha-hydroxycarboxylates" J Am Chem Soc 129:1278-1286.

Garnsey, Soya et al.: "Continuous glulcose detection using boronic acid-substituted viologens in, fluorescent hydrogels: linker effects and extension to fiber optics" Langmuir, ACS, Washington, DC vol. 22, No. 21, Oct. 10, 2006, pp. 9067-9074 (XP002442273ISSN: 0743-7463, compound (1) schemata 1,2 figure 1).

Gehrich, J. L., D. W. Lubbers, et al. (1986). "Optical fluorescence and its application to an intravascular blood gas monitoring system." IEE TBio-coed Eng BME-33: 117-132.

Hirata O. et al. 2002 "Allosteric saccharide sensing by a phenylboronic-acids-appended 5,15-bis(triarylethynyl)porphyrin" J Supramolecular Chemistry 2:133-142.

Hvastkovs, E. G., et al.: "Minor Groove Binding of a Novel Tetracationic Diviologen", Langmuir 2006, 22, 10821-10829.

(56) References Cited

OTHER PUBLICATIONS

Japanese First Office Action, re JP Application No. 2009-549167, dated Nov. 29, 2011.
Kostov, Y., P. Harms, et al. (2001). "Low-cost microbioreactor for high-throughput bioprocessing." Biotechnol Bioeng 72: 346-352.
Kuwabara, T., et al.: "Effect of Alkali Metal Ions on Photochromic Behavior of Bisviologen-incorporated Oligo-oxyethylene Units", Rapid Communication. Photochemistry and Photobiology, 2003, 77(5); 572-575.
Lakowitz et al., :"Optical sensing of glucose using phase-modulation fluorinntry," Analytica Chimica Acta, 271, (1993), 155-164.
Lee, S. K., et al.: "Conform~tion and binding properties of polymethylene-linked bisviologens-2-naphthol complexes", Journal of the Chemical Society, Perkin Transactions 2 2001, 1983-1988.
Lutty, G. A. (1978). "The acute intravenous toxicity of stains, dyes, and other fluorescent substances." Toxical Pharmacol. 44: 225-229.
Meadows and Schultz, "Design, manufacture and characterization of an optical fiber glucose affinity sensor based on an homogeneous fluorescence energy transfer assay system," (1993) Anal. Chim. Acta 280: pp. 21-30.
Mignani et al. "Biomedical sensors using optical fibres." Reports on Progress in Physics [online], Jan. 1996 [Retrieved on Nov. 15, 2010], vol. 59, No. 1, pp. 1-28, Retrieved from the internet: <URL http//iopscience.iop.org>.
Mohr, G. J. et al.: Application of a Novel Lipophilized Fluorescent dye in an Opitcal Nitrate Sensor, Journal of Fluorescence 1995, 5, 135-138.
Niu C.G. et al. "Fluorescence ratiometric pH sensor prepared from covalently immobilized porphyrin and benzothioxanthen e." 2005 Anal. Bioanal. Chem. 383(2):349-357.
Offenbacher, H., O. S. Wolfbeis, et al. (1986). "Fluorescence optical sensors for continuous determination of near-neutral pH values." Sensor Actuator 9: 73-84.
Park, Y. S., et al.: "Facile Reduction of ZeoliteOEncapsulated Viologens with Solvated Electrons and Selective Dispersion of Inter- and Intramolecular Dimers of Propylene-Bridged Bisviologen Radical Cation", LanQmuir 2000,16,4470-4477.
PCT International Search Report and Written Opinion re PCT/US2008/052204, dated May 27, 2008.
PCT International Search Report and Written Opinion re PCT/US2008/053226, dated Oct. 15, 2008.
PCT Partial Search Report re PCT/US2008/053226 dated Jun. 27, 2008.
PCT International Search Report re PCT/US2007/074255 dated Jul. 8, 2008 in 3 pages.
PCT Report on Patentability and Written Opinion re PCT/US2007/074255 dated Jan. 27, 2009 in 9 pages.
PCT International Preliminary Report on Patentability and Written Opinion re PCT/US2008/053097 dated Aug. 11, 2009.
PCT International Search Report re PCT/US2008/053097 dated Jun. 27, 2008.
PCT International Preliminary Report and Written Opinion re PCT/US2009/040379 dated Oct. 19, 2010.
PCT International Search Report (Declaration of Non-Establishment of ISR) and Written Opinion re PCT/US2009/040379 dated Aug. 4, 2009.
PCT Report on Patentability and Written Opinion re PCT/US2008/063332 dated Nov. 19, 2009.
PCT Partial International Search Report re PCT/US2008/063332 dated Oct. 20, 2008.
PCT International Preliminary Report on Patentabilitu re PCT/US2008/063330 dated Nov. 19, 2009.
PCT International Search Report and Written Opinion re PCT/US2008/063330 dated Sep. 3, 2008.
PCT International Preliminary Report on Patentability and Written Opinion re PCT/US2008/072359, dated Feb. 9, 2010.
PCT International Search Report and Written Opinion re PCT/US2008/072359 dated Dec. 15, 2008.
PCT Partial International Search Report re PCT/US2008/072359 dated Oct. 15, 2008.
PCT International Search Report and Written Opinion re PCT/US2008/062303 dated Aug. 14, 2008.
PCT International Search Report and Written Opinion re PCT/US2008/069855 dated Apr. 16, 2009.
PCT Preliminary Report re PCT/US2008/084239 dated May 25, 2010.
PCT International Search Report and Written Opinion re PCT/US2008/084239 dated Jan. 29, 2009.
PCT International Search Report and Written Opinion re PCT/US2010/044761, dated Oct. 6, 2010.
PCT International Search Report and Written Opinion re App. No. PCT/US10/61169, dated Mar. 1, 2011.
PCT International Search Report and Written Opinion re PCT/US2010/037502, dated Aug. 6, 2010.
PCT International Search Report and Written Opinion re PCT App. No. PCT/US 10/50910, dated Dec. 3, 2010.
PCT International Preliminary Report on Patentability and Written Opinion re PCT/US 10/50910 date of Issuance Apr. 3, 2012/date of mailing Apr. 12, 2012.
PCT International Search Report and Written Opinion re App. No. PCT/US 10/61163, dated Mar. 9, 2011.
PCT International Search Report and Written Opinion re App. No. PCT/US10/61173, dated Feb. 28, 2011.
PCT International Search Report and Written Opinion in App. No. PCT/US2011/028222, dated May 6, 2011, in 30 pages.
PCT Search Report and Written Opinion re PCT/US2011/023939, dated Jul. 27, 2011.
PCT International Search Report and Written Opinion re PCT/US2011/034167, mailed Jul. 29. 2011.
Peterson et al. "Fiber-optic for in vive measurement of oxygen partial pressure," Analytical Chemistry [online], Jan. 1984 [Retrieved on Nov. 15, 2010], vol. 57, No. 1, pp. 62-67, Retrieved from the Internet: <URL: http://pubs.acs.org>.
Sato, H., et al.: "Polymer Effect in Electrochromic Behavior of Oligomeric Viologens", Journal of Applied Polymer Science, vol. 24, 2075-2085 (1979).
Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170.
Sharrett, Z. et al. 2008 "Boronic acid-appended bis-viologens as a new family of viologen quenchers for glucose sensing" Tetrahedron Letters 49:300-304.
Song, A., S. Parus, et al. (1997) "High-performance fiber-optic pH microsensors for practical physiological measurements using a dual-emission sensitive dye." Analytical Chemistry 69: 863-867.
Sturdevant, M. F.: "How Sterilization Changes Long-Term Resin Properties", Plastics Engineering, Jan. 1991, pp. 27-32.
Suri, J. T. et al. 2003 "Continuous glucose sensing with a fluorescent thin-film hydrogel" Angew Chem Int Ed 42:5857-5859.
Suri, J. T. et al.: "Monosaccharide Detection with 4,7-Phenanthrolinium Salts: Charge-Induced Fuorescence Sensig", Langmuir 2003,19,5145-5152.
Takashinna, H., et al.: "Rema~l<ably stereoselective photoinduced electron-transfer reaction between zinc myoglobin and optically active binaphthyl bisviologen", Journal 0 Biological Inorganic Chemistry 2003, 8, 499-506.
The Immunoassay Handbook, pp. 1-618, ed. David Wild, Macmillan Press, 1994, United Kingdom.
Tsukahara, K., et al.: "Syntheses, Characterizations, and Redox Behavior of Optically Active Viologens and Bisviologens", Bulletin of the Chemical Society of Japan 1999, 72,139-149.
Turner N.G. et al. "Determination of the pH Gradient Across the Stratum Corneum." 1998 J. Investig. Dermatol. Symp. Proc. Aug. 3(2):110-3.
Wang, D. et al. 2001 "Ph()toh,Jnninescence quenching of conjugated macromolecules by bipyridinium derivatives in aqueous media: charge dependence" Langmuir 17:1262-1266.
Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314 (2): 119-124.

(56) References Cited

OTHER PUBLICATIONS

Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.

Zhang, S., S. Tanaka, et al. (1995). "Fibre-optical sensor based on fluorescent indicator for monitoring physiological pH values." Med Biol Eng Comput 33: 152-156.

Zhujun, Z. and W. R. Seitz (1984). "A fluorescence sensor for quantifying pH in the range from 6.5 to 8.5." Analytical Chimica Acta 160:47-55.

U.S. Reexamination, Request for Inter parties Reexamination, dated Sep. 6, 2012.

U.S. Transmittal of Communication toThird Party Requste Inter Partes Reexamination dated Oct. 22, 2012.

Angel, S. M., "Optrodes: Chemically Selective Fiber Optic Sensors," Spectoscopy, Apr. 1987, pp. 38-47.

Ayala et al., Database Caplus, DN 133:189758. (Protein Science (2000), 9(8), 1589-1593).

Badugu, R., et al.: "A Glucose sensing contact lens: A new approace to non-invasive continuous physiological glucose monitoring", SPIE Proceedings, The International Society for Optical Engineering—SPIE, Bellingha, Washington, USA, vol. 5317, Jan. 25, 2004.

Ballerstadt, Ralph, et al.: "Fluorescence Resonance Energy Transfer-Based Near-Infrared Fluorescence Sensor for Glucose Monitoring", Diabetes Technology & Therapeutics, vol. 6, No. 2, Apr. 1, 2004.

Bean & Johnson, 54 J. Am. Chem. Soc. 4415 (1932).

Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495.

Burnett, Peebles & Hageman, 96 Biochemical and Biophysical Research Communications 157 (1980).

Check, W., "ICUs tighten belts on blood glucose levels", Cap Today, Feb. 2005, in 7 pages, vol. 19-2, pp. 1,95-96,98,100,102, and 104 ("Check").

Choleau et al.: "Calibration of a subcutaneous amperometric glucose sensor implanted for 7 days in diabetic patients, Part 2. Superiority of the one-point calibration method." Biosensors and Bioelectrics, vol. 17, No. 8, Aug. 1, 2002.

Dawson, et al., 98 JACS 5996 (1970).

Definition of "cathether" from Webster's Ninth New Collegiate Dictionary, 1990, p. 216.

European Extended/Supplementary Search Report, re EP Application No. 10821254.9, dated Mar. 22, 2013.

Fidaleo et al., Database Caplus, DN 140:249134 (Chemical and Biochemical Engineering Quarterly (2003), 17(4), 311-318).

Forster, "Intermolecular Energy Transfer and Fluorescence, Annaten der Physik" (1948) pp. 55-75.

Furnary A.P. et al. "Effect of hyperglycemia and continuous intravenous insulin infusions on outcomes of cardiac surgical procedures: The Portland Diabetic Project", Endocrine Practice, Mar./Apr. 2004, pp. 21-33, vol. 10.

Gamoh, et al., 222 Analytica Chimica Acta 201 (1989).

Glazer, "The Time-Dependent Specific Interaction of 4-(4'-Anninophenylazo)Phenylarsonic Acid with Subtilisins," 59 Biochemistry 996 (1968).

Glazer, Chemical Abstracts, vol. 68, No. 23, Jun. 3, 1968, p. 111809 (total 3 pages).

Guilbault, George E., "Practical Fluorescence" (1973), pp. 599-600.

Hakkinen, Lajunen & Purokoski, A Potentiometric Study on the Complex Formation of Lactitol and Maltitol with Some Inorganic Oxyacids in Aqueous Solution, Chemical Abstracts, vol. 110, No. 83116f (1989).

Hakkinen, Purokoski & Lajunen, A Potentiometric Study on the Complex Formation of Germanic Acid and Germanate Ion with Sugar Acids and Disaccharides in Aqueous Solution, Chemical Abstracts, vol. 105, No. 233265s (1986).

Hayashi, et al., "Fluorometric measurement of glycosylated albumin in human serum," 149 Clinica Chimica Acta 149 (1985), 13-19 Elsevier.

Hirsch Irl B. et al. "Acute Complications of Diabetes" Endocrinology and Metabolism Clinics of North America, Dec. 2000, pp. 745-771, vol. 29-4.

Hirshfeld, "Reabsorption Sensing in Fluorescence Spectroscopy," UCRL Abstract No. 89736 ABST, published by Pittsberg Conference on Scientific Instrumentation, Mar. 1984.

Hunneche, "Antioxidant Activity of a Combinatorial Library of Emulsifier—Antioxidant Bioconjugates," J. Agric. Food Chem. 2008, 56, 9258-9268.

Kuraganov, B. I., et al.: Criterion for Hill equation validity for description of biosensor calibration curves, Analytica Chimica Acta, vol. 427, No. 1, Jan. 1, 2001.

Leijten FSS & DeWeerdt A W 1994 Critical illness polyneuropathy: a review of the literature, definition and pathophysiology. Clinical Neurology and Neurosurgery, 96: 10-19.

Levetan et al., "Hospital Management of Diabetes," in Acute Complications of Diabetes, vol. 29, No. 4, 745-71, at 745-54 (Dec. 2000).

Lindner, et al., 473 J. Chromatography 227-240 (1989).

Liu, et al., "Characterization of Immobilization of an Enzyme in a Modified Y Zeolite Matrix and Its Application to an Amperometric Glucose Biosensor," Anal. Chem. 1997, 69, pp. 2343-2348.

Medtronic, Features of the Guardian REAL-Time Continuous Glucose Monitoring System, Features that fit your diabetes management lifestyle, located at http://www.minimed.com/products/guardian/features.html on Aug. 28, 2007.

Mizock B A. Am J Med 1995; 98: 75-84.

Mosbach, Methods in Enzymology, vol. XLIV, 53 (1976).

Piper, Hannah G. "Real-Time Continuous Glucose Monitoring in Pediatric Patients During and After Cardiac Surgery," in Pediatrics, vol. 118, No. 3, Sep. 2006.

Purokoski, Lajunen & Hakkinen, A Potentiometric Study on the Complex Formation of Arsenious Acid, Arsenite Ion, Telluric Acid and Tellurate Ion with Sugar Acids and Disaccharides in Aqueous Solution, Chemical Abstracts, vol. 107, No. 122178n (1987).

Reyes-De-Corcuera, Josi et al.: "Enzyme-electropolynner-based amperometric biosensors: an innovative platform for time-temperature integrators." Journal of Agricultural and Food Chemistry, vol. 53, No. 23, Nov. 1, 2005.

Roy, et al., J. Inorg. Nucl. Chem., 106 (1957).

Seitz, "Chemical Sensors Based on Fiber Optics," Analytical Chemistry, vol. 56, pp. 16a-34a, 1984.

Snyder, et al., "The Preparation of Some Azo Boronic Acids," 70 J. Am. Chem. Soc. 232 (1948).

Stokes, et al.: "An optical oxygen sensor and reaction vessel for high-pressure applications", Limnol. Oceanogr., 44(1),1999,189-195.

Streitwieser, Jr. & Heathcock, Introduction to Organic Chemistry (1976).

Su et al., "Polyethersulfone Hollow Fiber Membranes for Hemodialysis," Progress in Hemodialysis—From Emergent Biotechnology to Clinical Practice, www.intechopen.com, Nov. 7, 2011. ISBN 978-953-307-377-4.

Udenfreund, "Fluorescence Assay in Biology and Medicine" (1962) pp. 108-109.

University of Santa Cruz, "Optical Glucose Sensor Holds Promise for Diabetics and Intensive Care Patients", Mar. 18, 2004, in 6 pages.

Van Den Berghe G., et al. "Intensive Insulin Therapy in the Medical ICU", The New England Journal of Medicine, Feb. 2, 2006, pp. 449-461, vol. 354-5.

Van Kempien & Kreuzer, "A Single-Unit Carbon Dioxide Sensing Microelectrode System," Respiration Physiology, (1975), 23, 371-379.

Vermeer, et al., 37 Tetr. Letters 3255 (1970).

Volker, Ludwig et al.: "Continuous Glucose Monitoring with Glucose Sensors: Calibration and Assessment Criteria", Diabetes Technology & Therapeutics, vol. 5, No. 4, Aug. 1, 2003.

Wilson, Intensive Insulin Therapy in Critical Care, Diabetes Care, Apr. 2007, pp. 1005-1011, vol. 30-4.

Zhujun, Z., et al. (1984). Analytical Chimica Acta 160:305-309.

Zisser, MD, et al. "Excitation: The use of Fluorescence in Glucose Monitoring (Part 11)," Glumetrics, Feb. 13, 2010.

(56) References Cited

OTHER PUBLICATIONS

Zochodne D W et al. 1987 Polyneuropathy associated with critical illness: a complication of sepsis and multiple organ failure. Brain, 110: 819-842.

Baldini "Invasive Sensors in Medicine." Optical Chemical Sensors, NATO Science Series 11: Mathematics, Physics and Chemistry [online], 2006 [Retrieved on Nov. 15, 2010], vol. 224, pp. 417-435, Retrieved from the Internet: <URL http:www.springerlink.com>.

Gott, "Heparin Bonding on Colloidal Graphite Surfaces," Department of Surgery, University of Wisconsin Medical School, Madison 6 Sciense, vol. 142, pp. 1297-1298, Dec. 6, 1963.

"Optical Glucose Sensor Holds Promise for Diabetics and Intensive Care Patients," in Science Daily, Mar. 18, 2004 (archived on Apr. 4, 2004 at: <http://web.archive.org/web/20040404161607/http://www.ScienceDaily.com/releases/2004/03/0403529.htm> ("ScienceDaily Article").

* cited by examiner

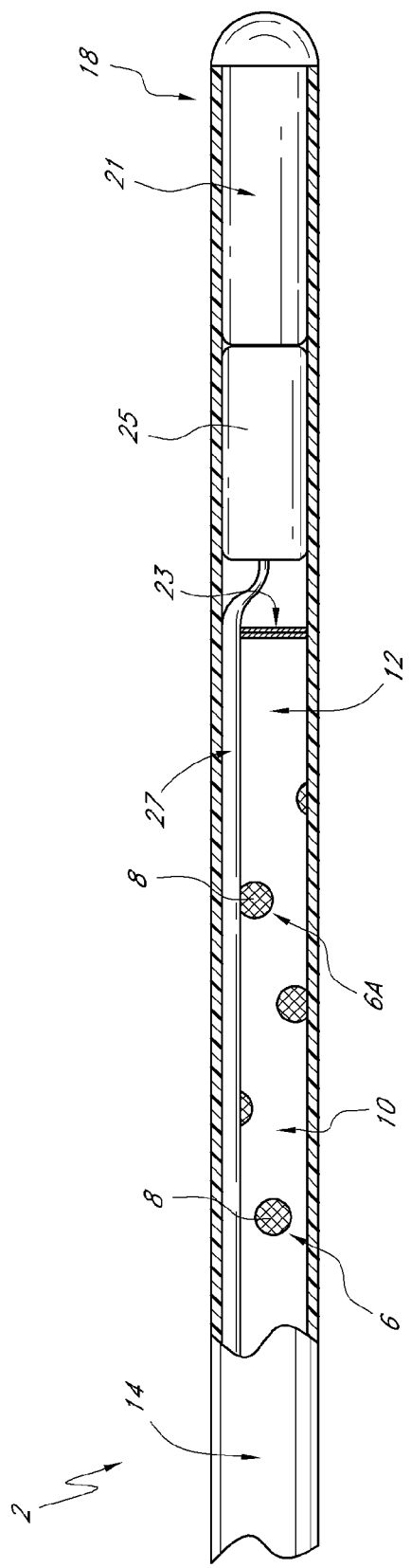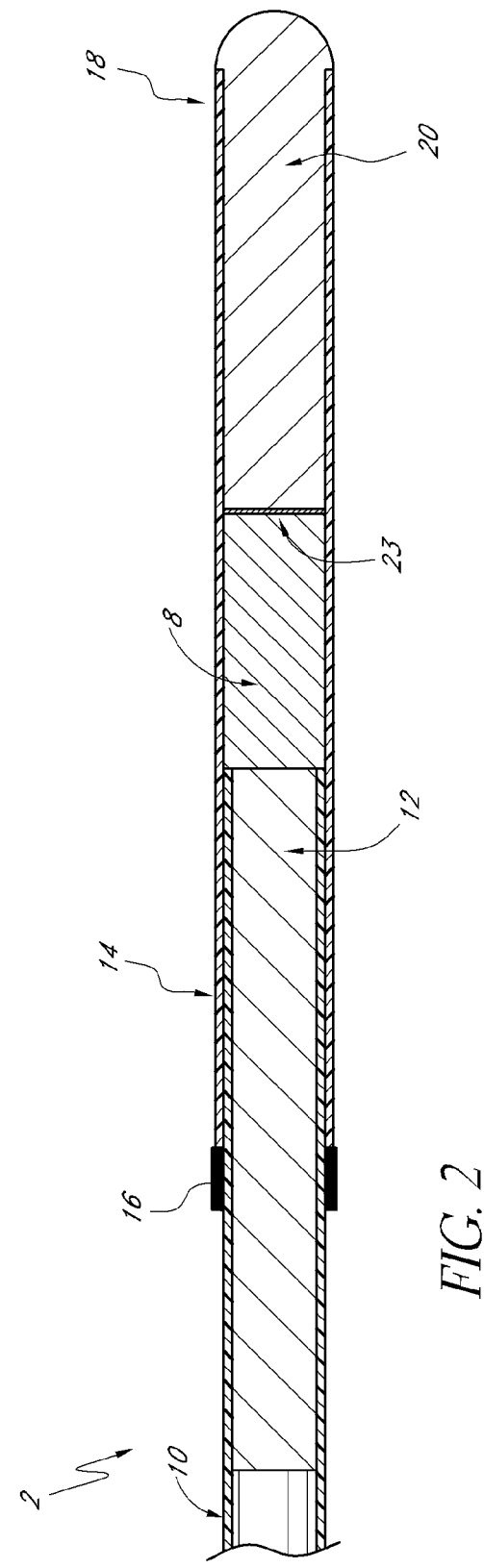

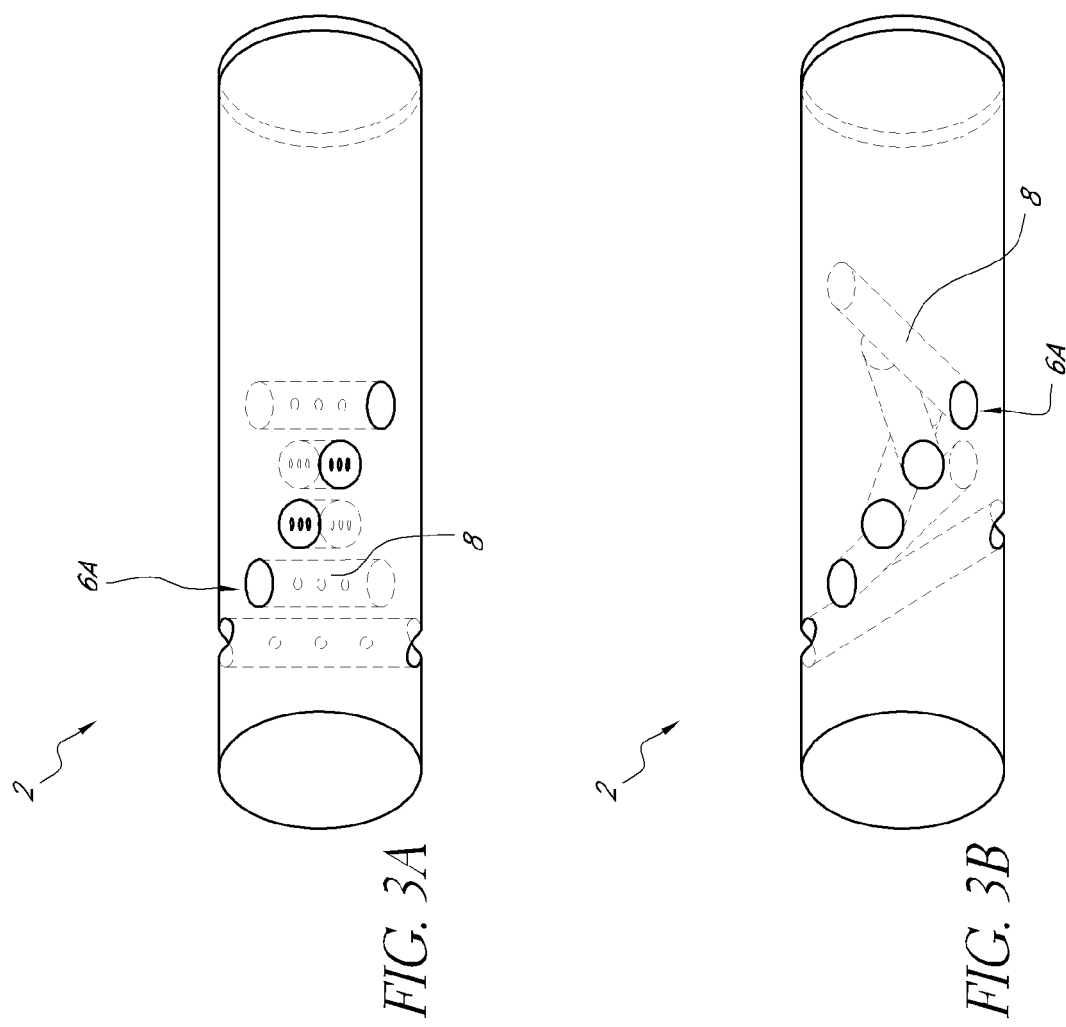

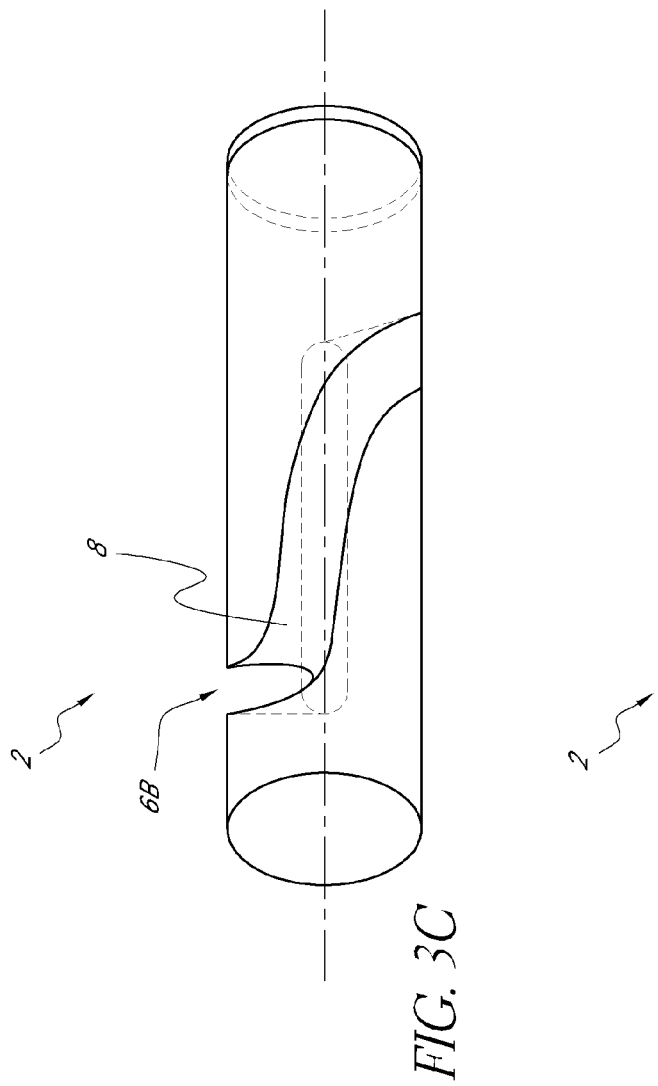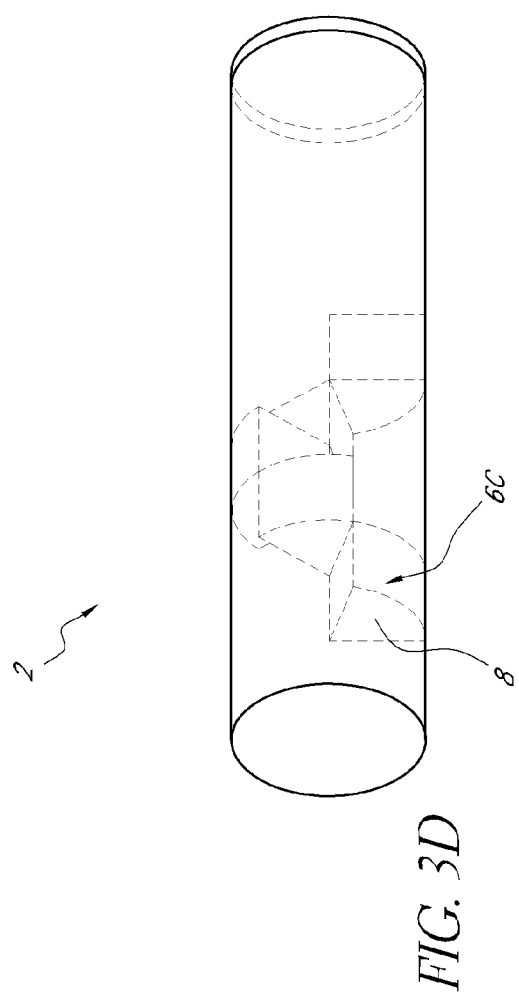

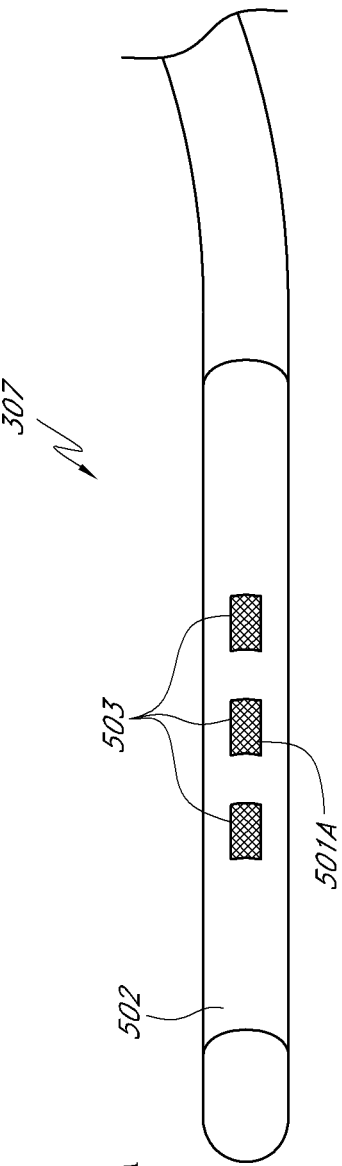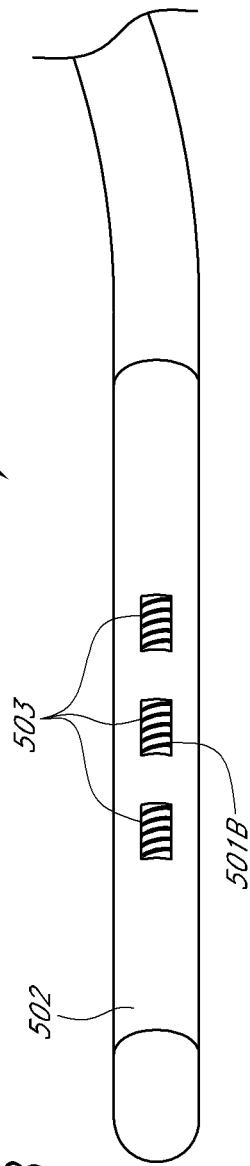
FIG. 6A
FIG. 6B

*Non-Porous Precursor Section*

*Microporous Membrane Section*

SENSORS WITH THROMBORESISTANT COATING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

Embodiments of the present invention generally relate to thromboresistant coatings for medical devices, such as intravascular glucose sensors, having a blood-contacting surface, as well as to methods for forming such coatings, and to the medical devices thus formed.

2. Description of the Related Art

Achieving glycemic control is facilitated by continuous or nearly continuous monitoring of patient blood glucose levels. One method for accomplishing such monitoring is through the use of an implanted glucose sensor. For example, an optical glucose sensor, such as those disclosed in U.S. Pat. Nos. 5,137,033, 5,512,246, 5,503,770, 6,627,177, 7,417,164 and 7,470,420, and U.S. Patent Publ. Nos. 2006/0083688, 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 61/045,887 (each of which is incorporated herein in its entirety by reference thereto), can be deployed in the vascular system of the patient, with glucose readings taken continuously, or as needed. Of course, any indwelling intravascular glucose sensor can potentially be used in monitoring glucose for the purpose of achieving glycemic control.

The presence of foreign bodies in the vascular system of patients, such as intravascular glucose sensors, can lead to the formation of a blood clot or thrombus around the sensor. In some cases, the thrombus can result in the restriction of blood flow through the blood vessel, impairing functionality of the sensor and/or health of the patient. In some cases, the thrombus can break off and travel through the bloodstream to other parts of the body, such as the heart or brain, leading to severe health problems. As result, it is desirable to minimize the formation of a thrombus on or near the sensor.

Heparin has been used clinically for decades as an intravenous anticoagulant to treat clotting disorders and to prevent thrombus formation during surgery and interventional procedures. Coating the outer surface of a medical device, e.g., stents, prostheses, catheters, tubing, and blood storage vessels, with heparin or a heparin containing complex (See, e.g., U.S. Reissued Pat. No. RE39,438 to Shah, et al.) may reduce the thrombogenecity of the device when it comes into contact with blood by: (1) inhibiting enzymes critical to the formation of fibrin (which holds thrombi together); (2) reducing the adsorption of blood proteins, which may lead to undesirable reactions on the device surface; and (3) reducing the adhesion and activation of platelets, which play an important role in thrombogenesis. Ideally, the heparin coating substantially shields the blood from the underlying surface of the medical device, such that the blood components contact the heparin coating rather than the device surface, thus reducing the formation of thrombi or emboli (blood clots that release and travel downstream).

Unfortunately, depending on the surface material of the device, heparin may not provide a lasting and/or contiguous thromboresistant coating. Various strategies have been implemented to enhance the integrity of the heparin coating. For example, photo-activated coupling methods can be used to covalently bind heparin to a device surface thereby extending the useful life of the coating (See e.g., Surmodics' PHOTO-LINK® process at www.surmodics.com/technologies-surface-biocompatibility-heparin.html). Alternatively, for certain materials, e.g., PVC, linkers such as tridodecylmethyl ammonium chloride (TDMAC) and PEO-polyethylene oxide, among others, have been used to space the heparin molecule away from the PVC surfaces (See e.g., U.S. Pat. No. 5,441,759 to Crouther et al.). Heparin may be cross-linked to polypeptides to create a thromboresistant hydrogel with peptide-specific functionality (See e.g., U.S. Pat. No. 7,303,814 to Lamberti, et al. disclosing a wound-healing functionality). Heparin derivatives or complexes, such as heparin benzalkonium chloride (hereinafter "HBAC"), have also been applied as a thromboresistant coating for medical devices. However, HBAC has not been used with success for devices, such as intravascular analyte sensors, that require passage of the analyte in the blood through the coating. Moreover, Hsu (U.S. Pat. No. 5,047,020) disclosed use of various heparin complexes for coating blood gas sensors and noted that the benzalkonium heparin complex was unsuitable for such an intravascular sensor.

Accordingly, there is an important unmet need for a thromboresistant coating and methods for applying such a coating to an intravascular analyte sensor, and in particular, a glucose sensor.

SUMMARY OF THE INVENTION

Embodiments of the invention relate to an analyte sensor, comprising: an elongate member; an analyte-responsive indicator disposed along a distal portion of the elongate member, wherein the indicator is capable of generating a signal related to a concentration of analyte in the blood vessel; a porous membrane covering at least the indicator along the distal portion of the elongate member; and a coating comprising heparin and benzalkonium stably associated with at least a portion of the porous membrane.

In preferred embodiments of the analyte sensor, the elongate member comprises an optical fiber comprising a light path. The analyte-responsive indicator preferably comprises a fluorophore operably coupled to an analyte binding moiety, wherein analyte binding causes a change in the emission intensity of the fluorophore, and wherein the analyte responsive indictor is disposed within the light path of the optical fiber. More preferably, the fluorophore is HPTS-triCysMA and the binding moiety is 3,3'-oBBV.

In certain embodiments, the porous membrane is a microporous membrane. The microporous membrane may comprise one or more polymers selected from a group consisting of the polyolefins, the fluoropolymers, the polycarbonates, and the polysulfones. More preferably, the microporous membrane comprises at least one fluoropolymer. The at least one fluoropolymer may be selected from the group consisting of polytetrafluoroethylene, perfluoroalkoxy polymer, fluorinated ethylene-propylene, polyethylenetetrafluoroethylene, polyvinylfluoride, polyethylenechlorotrifluoroethylene, polyvinylidene fluoride, polychlorotrifluoroethylene, perfluoropolyether, perfluoroelastomer, and fluoroelastomer.

In other embodiments of the analyte sensor, the microporous membrane comprises at least one polyolefin. The polyolefin is preferably polyethylene.

An equilibrium intravascular analyte sensor is disclosed in accordance with other embodiments of the invention. The equilibrium intravascular analyte sensor comprises: an optical fiber configured for positioning within a blood vessel and comprising a light path and an outer surface; a chemical indicator system comprising a fluorophore operably coupled to an analyte binding moiety, wherein the fluorophore and analyte binding moiety are immobilized within a water-insoluble organic polymer, and wherein the chemical indicator system is disposed within the light path along a distal portion of the optical fiber; and an antithrombogenic, analyte-permeable coating on at least a portion of the outer surface of the optical fiber and overlying the chemical indicator system disposed therein, wherein the coating comprises heparin covalently cross-linked to the outer surface.

The fluorophore is preferably HPTS-triCysMA and the binding moiety is preferably 3,3'-oBBV.

The equilibrium intravascular analyte sensor may further comprise a porous, analyte-permeable membrane disposed between the chemical indicator system and the antithrombogenic coating.

A method for reducing the thrombogenicity of an analyte sensor is disclosed in accordance with other embodiments of the invention. The method comprises: providing the analyte sensor comprising an elongate optical fiber defining a light path, an equilibrium fluorescent chemical indicator system disposed along a distal region of the optical fiber within the light path, and an analyte-permeable porous membrane, which forms an outer layer of at least a portion of the distal region, wherein the indicator system is covered by the porous membrane; contacting the analyte sensor with a single solution comprising a mixture of heparin and benzalkonium, or with separate first and second solutions, wherein the first solution comprises heparin and the second solution comprises benzalkonium; drying the analyte sensor; and repeating the contacting and drying steps between 2 and 10 times.

In preferred embodiments of the method, the equilibrium fluorescent chemical indicator system comprises a fluorophore and an analyte binding moiety, immobilized within a water-insoluble organic polymer. The fluorophore may be HPTS-triCysMA, the binding moiety may be 3,3'-oBBV, and the water-insoluble organic polymer may be a DMAA (N,N-dimethylacrylamide) hydrogel matrix.

In another embodiment of the invention, a method is disclosed for reducing the thrombogenicity of an analyte sensor. The method comprises: providing the analyte sensor comprising an elongate optical fiber defining a light path, an equilibrium fluorescent chemical indicator system disposed along a distal region of the optical fiber within the light path, and an analyte-permeable porous membrane, which forms an outer surface over at least a portion of the distal region, wherein the indicator system is covered by the porous membrane; providing a photoactivatable chemical linking agent and an antithrombogenic molecule, wherein the linking agent is capable, upon activation, of covalent attachment to the outer surface and the antithrombogenic molecule, wherein the linking agent comprises a charged, nonpolymeric di- or higher functional photoactivatable compound comprising two or more photoreactive groups and one or more charged groups; and activating the two or more photoreactive groups, thereby cross-linking the antithrombogenic molecule to the outer surface.

The equilibrium fluorescent chemical indicator system preferably comprises a fluorophore and an analyte binding moiety, immobilized within a water-insoluble organic polymer. In certain preferred embodiments of the method, the fluorophore is HPTS-triCysMA, the binding moiety is 3,3'-oBBV, and the water-insoluble organic polymer is a DMAA (N,N-dimethylacrylamide) hydrogel matrix.

In certain preferred embodiments of the method, the porous membrane comprises microporous polyethylene.

BRIEF DESCRIPTION OF THE DRAWINGS

FIG. 1 is a cut-away view of a sensor where a portion of the porous membrane sheath is cut away to expose the optical fiber and hydrogel beneath the membrane.

FIG. 2 is a cross-sectional view along a longitudinal axis of a sensor with a hydrogel disposed distal the optical fiber.

FIG. 3A shows a glucose sensor having a series of holes that form a helical configuration.

FIG. 3B shows a glucose sensor having a series of holes drilled or formed at an angle.

FIG. 3C shows a glucose sensor having at least one spiral groove.

FIG. 3D shows a glucose sensor having a series of triangular wedge cut-outs.

FIGS. 6A and 6B show alternative embodiments of an optical glucose sensor, wherein the optical sensor is surrounded by a tubular mesh (FIG. 6A) or coil (FIG. 6B), which is further surrounded by a polymeric material with an open window.

DETAILED DESCRIPTION OF THE PREFERRED EMBODIMENT

Figure 4:
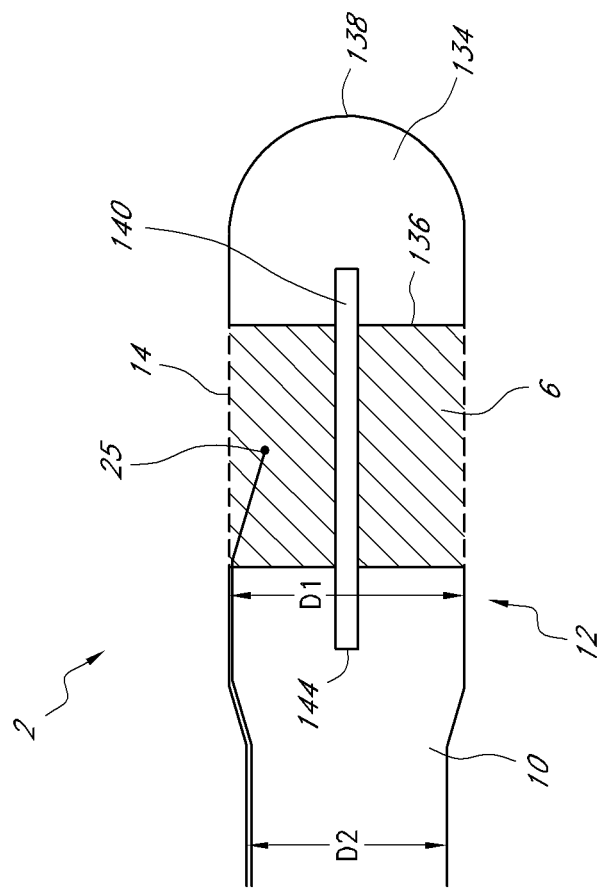
FIG. 4 shows a cross-sectional view of one embodiment of a glucose sensor having a cavity in the distal portion of the sensor.

The following description and examples illustrate a preferred embodiment of the present invention in detail. Those of skill in the art will recognize that there are numerous variations and modifications of this invention that are encompassed within its scope. Accordingly, the description of a preferred embodiment should not be deemed to limit the scope of the present invention.

Various embodiments disclosed herein are generally directed towards analyte sensors configured for in vivo deployment (e.g., intravascular, interstitial, etc.), preferably glucose sensors, wherein the sensors further comprise a thromboresistant outer surface, preferably a coating. Methods of coating sensors to create a thromoboresistant outer surface are also disclosed. Of course, intravascular sensors for detecting other analytes besides glucose may also benefit from aspects of the invention, e.g., reducing, inhibiting, and/or preventing blood clot or thrombus formation around the sensor.

DEFINITIONS

Unless defined otherwise, technical and scientific terms used herein have the same meaning as commonly understood by one of ordinary skill in the art to which this invention belongs. For purposes of the present invention, the following terms are defined below.

"Porous" is used herein to refer to material that has pores in it to allow permeation of chemical species through the material. The material can be "nanoporous" meaning the material has a mean pore diameter of less than about 2 nm. The material can be "microporous" meaning the material has a mean pore diameter between about 2 nm and about 50 nm. The material can be "mesoporous" meaning that the material has a mean pore diameter of greater than about 50 nm. The material can also be semipermeable, allowing only some chemical species to pass through while preventing or inhibiting other materials from passing through.

"Polyolefin" is used herein to refer to polymers produced from olefins, including copolymers. Two primary examples are polyethylene and polypropylene. Many different grades of these are available, with the grades frequently described in terms of molecular weight or density. Polymers from longer chain monomers than two or three carbons are also included.

"Fluoropolymer" is used herein to refer to polymers that contain chlorine and/or fluorine atoms. Examples include polytetrafluoroethylene, perfluoroalkoxy polymer, fluorinated ethylene-propylene, polyethylenetetrafluoroethylene, polyvinylfluoride, polyethylenechlorotrifluoroethylene, polyvinylidene fluoride, polychlorotrifluoroethylene, perfluoropolyether, perfluoroelastomer, and fluoroelastomer. These materials may be rigid or elastomeric. Trade names include TEFLON, TEFZEL, FLUON, TEDLAR, HALAR, KYNAR, KEL-F, CTFE, KALREZ, TECNOFLON, FFKM, VITON, FOMBLIN, and GALDEN.

"Polycarbonate" is used herein to refer to polymers having functional groups linked by carbonate groups. Trade names include LEXAN, CALIBRE, MAKROLON, PANLITE, and MAKROLIFE.

"Polysulfone" is used herein to refer to polymers containing the sulfone or sulfonyl group, and are most commonly made up of the subunit (aryl 1)-SO$_2$-(aryl 2).

"Heparin" as used herein includes polysaccharide materials having anticoagulant and/or antithrombotic properties, and is frequently referred to as containing alternating derivatives of D-glycocyamine (N-sulfated or N-acetylated) and uranic acid (L-iduronic acid with varying sulfate or D-glucuronic acid) joined by glycosidic linkages, or as including heterogeneous mixtures of variably sulfated polysaccharide chains composed of repeating units of D-glucosamine and either L-iduronic or D-glucuronic acids. Heparin can be derived from natural sources, such as bovine or porcine mucosal tissue, such as from the lung or intestine, and can have varying molecular weight.

"Benzalkonium chloride" is used herein to refer to halogen salts of quaternary ammonium compounds and mixtures of quaternary ammonium compounds primarily having a benzyl and three R-groups attached to the nitrogen, as depicted in the following structure:

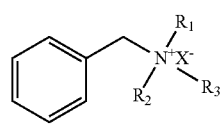

where R1 is in alkyl group having from about one to about five carbons, R2 is an alkyl group having about one to about five carbons, R3 is an alkyl group having about six to about 22 carbons, and X$^-$ is a halogen counterion. While the use of the word "chloride" refers to a specific halogen counter ion having atomic number 17, any halogen counter ion, such as fluoride, chloride, bromide, iodide, etc., with the most commonly used counter ion being chloride may be used in aspects of the present invention. Furthermore, "benzalkonium" is used herein to refer to the quaternary ammonium compound itself. Thus, the halogen salt "benzalkonium chloride" comprises "benzalkonium" and a chloride counter ion. "HBAC" is used herein to refer to complexes of heparin and benzalkonium chloride. Varying grades and molecular weights of heparin can be used. Varying grades of benzalkonium chloride, as well as other salts of benzalkonium ion having various chain lengths for the R-groups, whether in purified or mixed forms, or combined with other related or unrelated compounds can also be used.

Analyte Sensors

Analyte sensors suitable for coating with a thromboresistant surface include those analyte sensors having a polymeric external surface on at least a portion of the sensor. Preferably, that portion of the sensor is configured for in vivo deployment, and more preferably for intravascular deployment. Polymeric materials that can be utilized as a portion of the external surface include hydrophobic polymers such as polyolefins (for example polyethylene and polypropylene), polycarbonate, polysulfone, and fluorocarbons. In some embodiments, the polymeric material can be nanoporous. In some embodiments, the polymeric material can be microporous. In certain such embodiments, the mean pore diameter may be between about 2 nm and about 10 nm, or between about 10 nm and about 20 nm, or between about 20 nm and 30 nm, or between about 30 nm and about 40 nm, or between about 40 nm and about 50 nm, including combinations of the aforementioned ranges. Thus, for example, in certain embodiments, the mean pore diameter may be between about 10 nm and about 30 nm, or between about 20 nm and about 40 nm. In other embodiments, the polymeric material can be mesoporous.

In some embodiments, the porous polymeric surface can be a covering or sheath for at least a portion of the body of the sensor. When the polymeric surface is a covering or sheath, it can be made and/or applied by any suitable method. Sensors can be constructed in various ways, appropriate to the sensing chemistry/technique that is utilized by the sensor. In one embodiment, an optical sensor, such as a sensor producing a fluorescent response in relation to the analyte concentration can have a porous polymeric outer surface for at least a portion of the sensor assembly.

In some embodiments, a sensor can include an insoluble polymeric matrix, which immobilizes the analyte sensitive chemical indicator systems and is sufficiently permeable to the analyte of interest. Suitable polymeric matrix materials include those related to acrylic polymers. In some embodiments, fluorophores and/or binders/quenchers can be incorporated into the polymeric matrix (See e.g., U.S. Pat. Nos. 6,627,177, 7,470,420 and 7,417,164; each of which is incorporated herein in its entirety by reference).

Any other intravascular glucose sensor may be used in accordance with embodiments of the invention, including for example the electrochemical sensors disclosed in U.S. Publication Nos. 2008/0119704, 2008/0197024, 2008/0200788, 2008/0200789 and 2008/0200791.

Preferred embodiments of the glucose sensor are configured for implantation into a patient. For example, implantation of the sensor may be made in the arterial or venous systems for direct testing of glucose levels in blood. The site of implantation may affect the particular shape, components, and configuration of the sensor. In some embodiments, the sensor may be configured for interstitial deployment.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902; each of which is incorporated herein in its entirety by reference thereto.

Other glucose sensors configured for intravascular deployment include electrochemical sensors, such as those disclosed in U.S. Patent Publ. Nos. 2008/0119704, 2008/0197024, 2008/0200788, 2008/0200789 and 2008/0200791; each of which is incorporated herein in its entirety by reference thereto.

An optical glucose sensor in accordance with preferred embodiments of the present invention comprises a chemical indicator system. Some useful indicator systems comprise a fluorophore operably coupled to an analyte binding moiety, wherein analyte binding causes an apparent optical change in the fluorophore concentration (e.g., emission intensity). For example, a glucose binding moiety such as 3,3'-oBBV that is operably coupled to a fluorescent dye such as HPTS-tri-CysMA will quench the emission intensity of the fluorescent dye, wherein the extent of quenching is reduced upon glucose binding resulting in an increase in emission intensity related to glucose concentration. In further preferred embodiments, the indicator systems also comprise a means for immobilizing the sensing moieties (e.g., dye-quencher) such that they remain physically close enough to one another to react (quenching). Such immobilizing means are preferably insoluble in an aqueous environment (e.g., intravascular), permeable to the target analytes, and impermeable to the sensing moieties. Typically, the immobilizing means comprises a water-insoluble organic polymer matrix. For example, the HPTS-triCysMA dye and 3,3'-oBBV quencher may be effectively immobilized within a DMAA (N,N-dimethylacrylamide) hydrogel matrix.

Some preferred fluorophores (e.g., HPTS-triCysMA), quenchers/analyte binding moieties (e.g., 3,3'-oBBV) and immobilizing means (e.g., N,N-dimethylacrylamide), as well as methods for synthesizing and assembling such indicator systems are set forth in greater detail in U.S. Pat. Nos. 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 12/187,248, 12/172,059, 12/274,617 and 12/424,902.

Other indicator chemistries, such as those disclosed in U.S. Pat. No. 5,176,882 to Gray et al. and U.S. Pat. No. 5,137,833 to Russell, can also be used in accordance with embodiments of the present invention; both of which are incorporated herein in their entireties by reference thereto. In some embodiments, an indicator system may comprise an analyte binding protein operably coupled to a fluorophore, such as the indicator systems and glucose binding proteins disclosed in U.S. Pat. Nos. 6,197,534, 6,227,627, 6,521,447, 6,855,556, 7,064,103, 7,316,909, 7,326,538, 7,345,160, and 7,496,392, U.S. Patent Application Publication Nos. 2003/0232383, 2005/0059097, 2005/0282225, 2009/0104714, 2008/0311675, 2008/0261255, 2007/0136825, 2007/0207498, and 2009/0048430, and PCT International Publication Nos. WO 2009/021052, WO 2009/036070, WO 2009/021026, WO 2009/021039, WO 2003/060464, and WO 2008/072338 which are hereby incorporated by reference herein in their entireties.

FIG. 1 shows a sensor 2 in accordance with an embodiment of the present invention. The sensor comprises an optical fiber 10 with a distal end 12 disposed in a porous membrane sheath 14. The optical fiber 10 has cavities, such as holes 6A, in the fiber optic wall that can be formed by, for example, mechanical means such as drilling or cutting. The holes 6A in the optical fiber 10 can be filled with a suitable compound, such as a polymer. In some embodiments, the polymer is a hydrogel 8. In other embodiments of the sensor 2 as shown in FIG. 2, the optical fiber 10 does not have holes 6A, and instead, the hydrogel 8 is disposed in a space distal to the distal end 12 of the optical fiber 10 and proximal to the mirror 23. In some embodiments, the sensor 2 is a glucose sensor. In some embodiments, the glucose sensor is an intravascular glucose sensor.

In some embodiments, the porous membrane sheath 14 can be made from a polymeric material such as polyethylene, polycarbonate, polysulfone or polypropylene. Other materials can also be used to make the porous membrane sheath 14 such as zeolites, ceramics, metals, or combinations of these materials. In some embodiments, the porous membrane sheath 14 may be nanoporous. In other embodiments, the porous membrane sheath 14 may be microporous. In still other embodiments, the porous membrane sheath 14 may be mesoporous.

In some embodiments as shown in FIG. 2, the porous membrane sheath 14 is attached to the optical fiber 10 by a connector 16. For example, the connector 16 can be an elastic collar that holds the porous membrane sheath 14 in place by exerting a compressive force on the optical fiber 10, as shown in FIG. 2. In other embodiments, the connector 16 is an adhesive or a thermal weld.

In some embodiments as shown in FIG. 1, a mirror 23 and thermistor 25 can be placed within the porous membrane sheath 14 distal the distal end 12 of the optical fiber 10. Thermistor leads 27 can be made to run in a space between the optical fiber 10 and porous membrane sheath 14. Although a thermistor 25 is shown, other devices such as a thermocouple, pressure transducer, an oxygen sensor, a carbon dioxide sensor or a pH sensor for example can be used instead.

In some embodiments as shown in FIG. 2, the distal end 18 of the porous membrane sheath 14 is open and can be sealed with, for example, an adhesive 20. In some embodiments, the adhesive 20 can comprise a polymerizable material that can fill the distal end 18 and then be polymerized into a plug. Alternatively, in other embodiments the distal end 18 can be thermally welded by melting a portion of the polymeric material on the distal end 18, closing the opening and allowing the melted polymeric material to resolidify. In other embodiments as shown in FIG. 1, a polymeric plug 21 can be inserted into the distal end 18 and thermally heated to weld the plug to the porous membrane sheath 14. Themoplastic polymeric materials such as polyethylene, polypropylene, polycarbonate and polysulfone are particularly suited for thermal welding. In other embodiments, the distal end 18 of the porous membrane sheath 14 can be sealed against the optical fiber 10.

After the porous membrane sheath 14 is attached to the optical fiber 10 and the distal end 18 of the porous membrane sheath 14 is sealed, the sensor 2 can be vacuum filled with a first solution comprising a monomer, a crosslinker and a first initiator. Vacuum filling of a polymerizable solution through a porous membrane and into a cavity in a sensor is described in detail in U.S. Pat. No. 5,618,587 to Markle et al.; incorporated herein in its entirety by reference thereto. The first solution is allowed to fill the cavity 6 within the optical fiber 10.

In some embodiments, the first solution is aqueous and the monomer, the crosslinker and the first initiator are soluble in water. For example, in some embodiments, the monomer is acrylamide, the crosslinker is bisacrylamide and the first initiator is ammonium persulfate. In other embodiments, the monomer is dimethylacrylamide or N-hydroxymethylacrylamide. By increasing the concentrations of the monomer and/or crosslinker, the porosity of the resulting gel can be decreased. Conversely, by decreasing the concentrations of the monomer and/or crosslinker, the porosity of the resulting gel can be increased. Other types of monomers and crosslinkers are also contemplated. In other embodiments, the first solution further comprises an analyte indicator system comprising a fluorophore and an analyte binding moiety that functions to quench the fluorescent emission of the fluorophore by an amount related to the concentration of the analyte. In some embodiments, the fluorophore and analyte binding moiety are immobilized during polymerization, such that the fluorophore and analyte binding moiety are operably coupled. In other embodiments, the fluorophore and analyte binding moiety are covalently linked. The indicator system chemistry may also be covalently linked to the polymeric matrix.

In some embodiments, after the sensor 2 is filled with the first solution, the optical fiber 10 and the first solution filled porous membrane sheath 14 and cavity 6 are transferred to and immersed into a second solution comprising a second initiator. In some embodiments, the second solution is aqueous and the second initiator is tetramethylethylenediamine (TEMED). In some embodiments, the second solution further comprises the same fluorescent dye and/or quencher found in the first solution and in substantially the same concentrations. By having the fluorescent dye and quencher in both the first solution and the second solution, diffusion of fluorescent dye and quencher out of the first solution and into the second solution can be reduced. In some embodiments where a second solution is used, the second solution further comprises monomer in substantially the same concentration as in the first solution. This reduces diffusion of monomer out of the first solution by reducing the monomer gradient between the first solution and the second solution.

In some embodiments, at or approximately at the interface between the first and second solutions, the first initiator and the second initiator can react together to generate a radical. In some embodiments, the first initiator and the second initiator react together in a redox reaction. In other embodiments, the radical can be generated by thermal decomposition, photolytic initiation or initiation by ionizing radiation. In these other embodiments, the radical may be generated anywhere in the first solution. Once the radical is generated, the radical can then initiate polymerization of the monomer and crosslinker in the first solution.

When the radical is generated via a redox reaction as described herein, the polymerization proceeds generally from the interface between the first and second solutions to the interior of the porous membrane sheath 14 and towards the cavity in the optical fiber 10. Rapid initiation of polymerization can help reduce the amount of first initiator that can diffuse from the first solution and into the second solution. Reducing the amount of first initiator that diffuses out of the first solution helps reduce polymerization of monomer outside the porous membrane sheath 14 which helps in forming a smooth external surface. Polymerization of the monomer and crosslinker results in a hydrogel 8 that in some embodiments substantially immobilizes the indicator system, forming the sensor 2. Further variations on polymerization methodologies are disclosed in U.S. Patent Publ. No. 2008/0187655; incorporated herein in its entirety by reference thereto.

With reference to FIG. 3A, in certain embodiments, the glucose sensor 2 is a solid optical fiber with a series holes 6A drilled straight through the sides of the optical fiber. In certain embodiments, the holes 6A are filled with the hydrogels 8. In certain embodiments, the series of holes 6A that are drilled through the glucose sensor 2 are evenly spaced horizontally and evenly rotated around the sides of the glucose sensor 2 to form a spiral or helical configuration. In certain embodiments, the series of holes 6A are drilled through the diameter of the glucose sensor 2. With reference to FIG. 3B, in certain embodiments, the glucose sensor 2 is a solid optical fiber with a series of holes 6A drilled through the sides of the fiber at an angle. In certain embodiments, the series of holes 6A drilled at an angle, which are filled with hydrogel 8, are evenly spaced horizontally and evenly rotated around the sides the glucose sensor 2. With reference to FIG. 3C, in certain embodiments, the optical fiber comprises a groove 6B along the length of the optical fiber, wherein the groove 6B is filled with hydrogel 8. In certain embodiments, the depth of the groove 6B extends to the center of the optical fiber. In certain embodiments, the groove 6B spirals around the optical fiber. In certain embodiments, the groove 6B spirals around the optical fiber to complete at least one rotation. In certain embodiments, the groove spirals 6B around the optical fiber to complete multiple rotations around the optical fiber.

With reference to FIG. 3D, in certain embodiments, the glucose sensor 2 is a solid optical fiber with triangular wedges 6C cut from the fiber. In certain embodiments, the triangular wedge areas 6C are filled with hydrogel 8. In certain embodiments, the triangular wedges cut-outs 6C are evenly spaced horizontally and around the sides of the glucose sensor 2. In certain embodiments, all light traveling in the glucose sensor 2 is transmitted through at least one hole 6A or groove 6B filled with hydrogel 8.

In certain embodiments, as illustrated in FIG. 4, the glucose sensor 2 comprises an optical fiber 10 having a distal end 12, an atraumatic tip portion 134 having a proximal end 136 and a distal end 138, a cavity 6 between the distal end 12 of the optical fiber 10 and the proximal end 136 of the atraumatic tip portion 134, and a rod 140 connecting the distal end 12 of the optical fiber 10 to the proximal end 136 of the atraumatic tip portion 134. A hydrogel 8 containing glucose sensing chemistry, for example a fluorophore and quencher, fills the cavity 6. Covering the hydrogel filled cavity 6 is a selectively permeable membrane 14 that allows passage of glucose into and out of the hydrogel 8. Although these embodiments are described using a glucose sensor 2, it should be understood by a person of ordinary skill in the art that the sensor 2 can be modified to measure other analytes by changing, for example, the sensing chemistry, and if necessary, the selectively permeable membrane 14. The proximal portion of the sensor 2 comprises the proximal portion of the optical fiber 10. In some embodiments, the diameter, D1, of the distal portion of the sensor 2 is greater than the diameter, D2, of the proximal portion of the sensor 2. For example, the diameter D1 of the distal portion of the sensor 2 can be between about 0.0080 inches and 0.020 inches, while the diameter D2 of the proximal portion of the sensor 2 can be between about 0.005 inches to 0.015 inches. In some embodiments, the diameter D1 of the distal portion of the sensor 2 is about 0.012 inches, while the diameter D2 of the proximal portion of the sensor 2 is about 0.010 inches.

In some embodiments, the glucose sensor 2 includes a temperature sensor 25, such as thermocouple or thermistor. The temperature sensor 25 can measure the temperature of the hydrogel 8 and glucose sensing chemistry system. The temperature sensor 25 is particularly important when the glucose sensing chemistry, such as a fluorophore system, is affected by temperature change. For example, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of glucose concentration, as more fully described below.

In certain embodiments, the hydrogels are associated with a plurality of fluorophore systems. In certain embodiments, the fluorophore systems comprise a quencher with a glucose receptor site. In certain embodiments, when there is no glucose present to bind with the glucose receptor, the quencher prevents the fluorophore system from emitting light when the dye is excited by an excitation light. In certain embodiments, when there is glucose present to bind with the glucose receptor, the quencher allows the fluorophore system to emit light when the dye is excited by an excitation light.

In certain embodiments, the emission produced by the fluorophore system varies with the pH of the solution (for example, blood), such that different excitation wavelengths (one exciting the acid form of the fluorophore and the other the base form of the fluorophore) produce different emissions signals. In preferred embodiments, the ratio of the emission signal from the acid form of the fluorophore over the emission signal from the base form of the fluorophore is related to the pH level of the blood; the simultaneous measurement of glucose and pH is described in detail in U.S. Patent Publication No. 2008/0188722 (incorporated herein in its entirety by reference thereto). In certain embodiments, an interference filter is employed to ensure that the two excitation lights are exciting only one form (the acid form or the base form) of the fluorophore.

Figure 5:
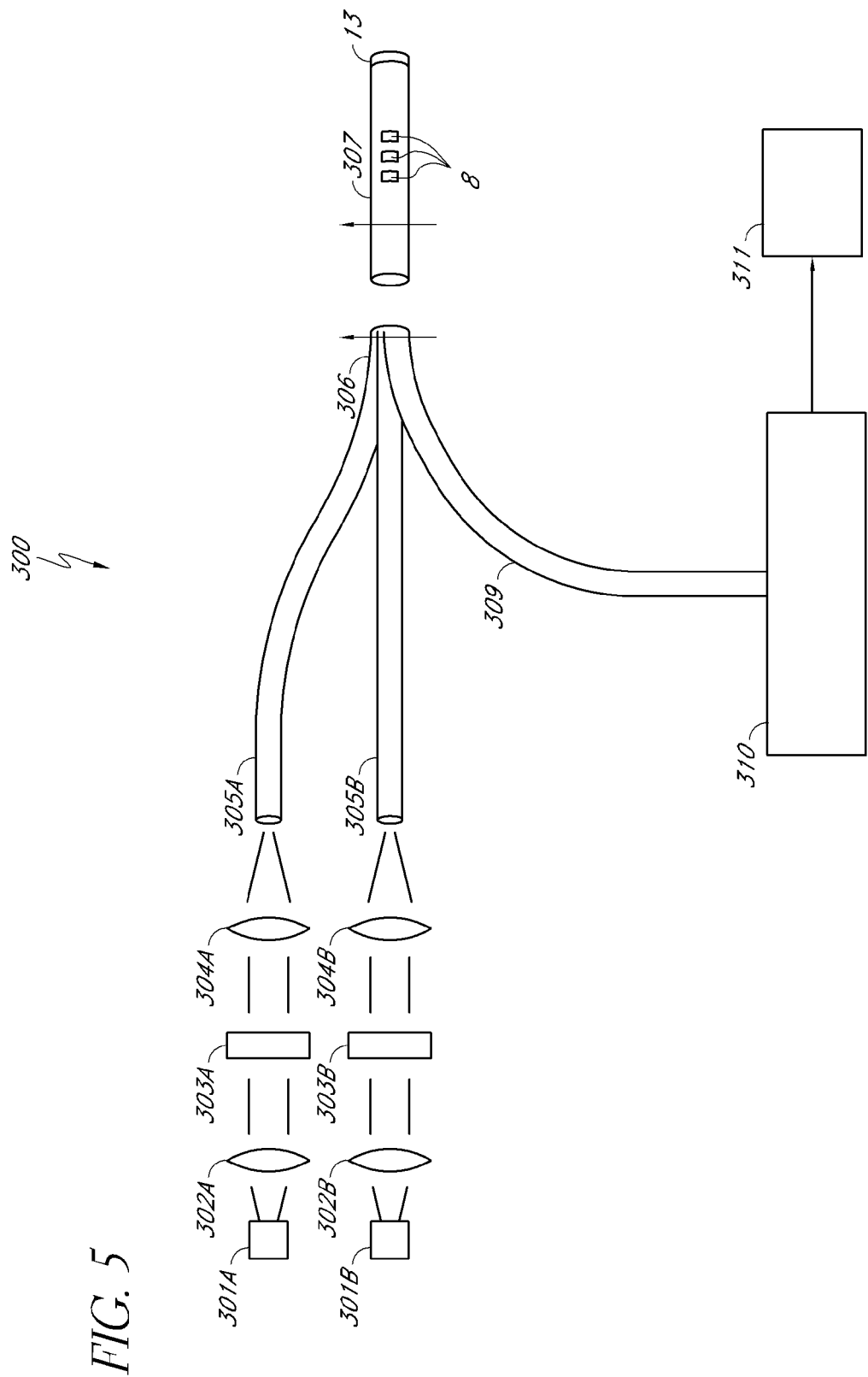
FIG. 5 shows a glucose measurement system comprising two excitation light sources and a microspectrometer and/or spectrometer.

Variations optical sensing systems, light sources, hardware, filters, and detection systems are described in detail in U.S. Publication No. 2008/0188725; incorporated herein in its entirety by reference thereto. See e.g., FIG. 5, wherein certain embodiments comprise at least two light sources. In certain embodiments, the light sources 301A, 301B generate excitation light that is transmitted through a collimator lens 302A, 302B. In certain embodiments, the resulting light from collimator lens 302A, 302B is transmitted to interference filters 303A, 303B. In certain embodiments, the resulting light from interference filters 303A, 303B is focused by focusing lens 304A, 304B into fiber optic lines 305A, 305B. In certain embodiments, fiber optic lines may be a single fiber or a bundle of fibers. In certain embodiments, the fiber optic line 309 may be a single fiber or a bundle of fibers. In certain embodiments, fiber optic lines 305A, 305B, 309 are bundled together at junction 306 and are connected at glucose sensor 307. The glucose sensor 307 comprises hydrogels 8.

In certain embodiments, the emission light and the excitation light are reflected off the mirror 13 and into the fiber optic line 309. In certain embodiments, the fiber optic line 309 is connected to microspectrometer 310 that measures the entire spectrum of light in the glucose measurement system 300. The microspectrometer 310 may be coupled to a data processing module 311, e.g., the sensor control unit and/or receiver/display unit. In certain embodiments, the ratio of emission light over the corresponding excitation light is related to the concentration of glucose. In certain embodiments, the ratio of the emissions light (for example, the acid form) produced by the first excitation light over the emission light (for example, the base form) produced by the second excitation light is related to pH levels in the test solution, for example blood.

In certain preferred embodiments, the microspectrometer is the UV/VIS Microspectrometer Module manufactured by Boehringer Ingelheim. Any microspectrometer can be used. Alternatively, the microspectrometer could be substituted with other spectrometer, such as those manufactured by Ocean Optic Inc.

In certain embodiments described above, the ratiometric calculations require measurements of various light intensities. In certain embodiments, these measurements are determined by measuring the peak amplitudes at a particular wavelength or wavelength band. In certain embodiments, these measurements are determined by calculating the area under the curve between two particular wavelengths as for example with the output from a microspectrometer.

With reference to FIGS. 6A and 6B, another embodiment of an intravascular optical glucose sensor is illustrated; this sensor configuration is disclosed in greater detail in WO2009/019470 (incorporated herein in its entirety by reference thereto). To provide a stronger and more robust sensor, which can withstand the pressures of being introduced into the body, yet retain some flexibility, sensors have been developed with internal reinforced walls, such as those depicted in FIGS. 6A and 6B. FIG. 6A shows a tube having a densely packed mesh 501A made of a first material and coated with an outer wall 502 of a second material. Three square cutouts 503 in the outer wall 502 of the tube arranged in a line can be seen in FIG. 6A, but cutouts of other shapes, positioned in other arrangements, are clearly feasible, depending on the embodiments. In the illustrated embodiment, the mesh 501A shows a high density of filament crossovers. This embodiment therefore has an increased strength and a reduced porosity. The braid is able to provide strength to the sensor, while allowing the tubular structure to flex and be maneuvered to the correct sensing position.

FIG. 6B depicts an embodiment in which the first material is in the form of a coil 501B which is coated with an outer wall 502 of the second material. Similar to FIG. 6A, three square cutouts 503 in the outer wall 502 of the tube arranged in a line can be seen in FIG. 6B, but cutouts of other shapes, positioned in other arrangements, are clearly feasible, depending on the embodiments. In this embodiment, the coil 501B is densely packed, providing increased strength and reduced porosity in a similar manner to the embodiment depicted in FIG. 6A. The reinforced walls can be provided in a number of ways, for example by providing a braided tubular structure which contains the sensing apparatus, as described in International patent publication WO2004/054438; incorporated herein in its entirety by reference thereto.

The first material is in the form of a mesh 501A, the density of filament crossovers may be varied in order to control the properties of the resulting tube. For example, a high density mesh may have greater strength and a low density mesh a greater flexibility. Variation in mesh density will also vary the porosity of the mesh. This is significant at the location of the opening in the outer wall since the porosity of the mesh will control the speed of diffusion of the material to be tested into the tube. Variation in the tightness of a coil can provide a similar effect.

The second material is used to coat the first material in order to form a continuous substantially impermeable outer wall 502 of the hollow tube. As used herein, the phrase substantially impermeable means that the second material forms an effectively closed tube, which is impermeable to the ingress of material from outside the tube to inside the tube. Accordingly, until a portion of the second material is removed, the tube is effectively sealed along its length, except, in some embodiments, at its ends.

Suitable materials for use as the second material generally include polymeric materials, more particularly polyesters, polyolefins such as polyethylene (PE), e.g. low density polyethylene (LDPE), fluoropolymers such as fluorinated ethylene propylene (FEP), polytetrafluoroethylene (PTFE) and perfluoroalkoxy polymer (PFA), polyvinylchloride (PVC), polyamides such as polyether block amide (PEBA), Pebax®, nylon and polyurethane. Polyesters and polyolefins are preferred due to their suitability for extrusion over the coil 501B or tubular mesh 501A. The selective removal of a portion of a polyester or polyolefin coating, e.g. by laser ablation, is also straightforward. Polyolefins are particularly preferred due to the ease of laser ablating these materials.

In order to form a continuous substantially impermeable tube prior to selective removal of a portion of the second material, the second material is first used to coat the coil or tubular mesh formed by the first material. The second material can either coat the outer surfaces of the first material, and in effect form a continuous substantially impermeable tube around the coil or tubular mesh formed by the first material, or the second material can entirely encapsulate the first material, effectively forming a tube of the second material in which is embedded the coil or tubular mesh formed by the first material. In one embodiment the second material can be applied to the first material by dip coating the coil or tubular mesh formed by the first material. In this embodiment, the second material is probably a polyamide, which results in a very stiff tube. In another embodiment, a tube of the second material can be provided, around which is formed the coil or tubular mesh of the first material. A further layer of the second material is then applied over the first material, resulting in the first material being sandwiched between two layers of the second material.

In a preferred embodiment, the first material is metallic and the second material is polymeric. In addition to the first and second materials, it is possible to include further materials in the tubes of the invention. For example, for some applications it may be useful to include a radiopaque additive to enable the sensor incorporating the tube to be visible in vivo. For example, radiopaque additives such as barium sulfate, bismuth subcarbonate, bismuth trioxide and tungsten can be added. Where present, these are preferably doped within the second material.

In certain processes, a portion of the second material is selectively removed in order to generate at least one opening in a region of the outer wall, while retaining the first material in that region. As the first material is present in the form of a coil or a tubular mesh, the first material does not form a completely closed tube. Accordingly, when the second material is removed in said region, this effectively forms a break in the continuous substantially impermeable wall of the tube. Where the second material simply coats the first material, it is necessary simply to remove the coating provided by this second material in the region where the opening is to be formed. Where the second material effectively encapsulates the first material, it is necessary to remove all of the second material which surrounds and encapsulates the first material in the region where the opening is to be formed.

Preferably, the chemical indicator system of the sensor is located adjacent to the opening formed by selective removal of the second material. This allows sensing of the environment in the region of the opening on the tube wall. For example, where the sensor is a glucose sensor, glucose is able to pass from the blood vessel or other cavity where the sensor is introduced through the opening and into the tube where its presence can be detected and measured by the probe.

The size of the opening in the outer wall will generally be between 1 and 400 $mm^2$, for example between 25 and 225 $mm^2$. The size of the opening must not be too small otherwise the blood or other substance into which the sensor is introduced will not be able to pass through the opening or will pass through in insufficient quantities for an accurate measurement to be made. The opening must also be large enough to allow positioning of the probe such that it is adjacent to the opening, even if it moves slightly when the sensor is introduced into the body.

In one embodiment, only one opening is generated in the tube wall, i.e. only one region of the second material is selectively removed. Preferably the opening extends only a portion of the way around the circumference of the tube. In one embodiment, it is preferred to retain some continuity of the second material along the entire length of the tube, and is hence preferred that the opening does not extend fully around the circumference of the tube. For example, it may be preferred that the opening extends around up to a maximum 75%, more preferably up to 50%, of the circumference of the tube. In another embodiment of the invention, a plurality of openings can be generated in the tube wall, i.e. more than one region of the second material can be selectively removed. This embodiment allows for probes to be located at a number of points along the length of the tube, and for multiple measurements to be taken. Thus, it is possible for a number of probes to be located within the tube, each tube being adjacent to a different opening within the tube wall. Alternatively, a single probe could be located within the tube and be provided with means for moving it from one opening to another opening, hence allowing measurements to be taken at a number of points along the length of the tube.

Thromboresistant Coatings

Molecules of a biocompatible agent are attached to the surfaces of the medical device to improve biocompatibility, such as antithrombogenic agents like heparin, albumin, streptokinase, tissue plasminogin activator (TPA) or urokinase. For example, the biocompatible agent may comprise molecules of both albumin and heparin. In one embodiment the molecules of a biocompatible material are joined to one another to form a film that is attached to a solid surface by a linking moiety. In other examples, various surface treatments of the optical glucose sensor can be used, such as those disclosed in U.S. Pat. Nos. 4,722,906, 4,973,493, 4,979,959, 5,002,582, 5,049,403, 5,213,898, 5,217,492, 5,258,041, 5,512,329, 5,563,056, 5,637,460, 5,714,360, 5,840,190, 5,858,653, 5,894,070, 5,942,555, 6,007,833, 6,090,995, 6,121,027, 6,254,634, 6,254,921, 6,278,018, 6,410,044, 6,444,318, 6,461,665, 6,465,178, 6,465,525, 6,506,895, 6,559,132, 6,669,994, 6,767,405, 7,300,756, 7,550,443, 7,550,444, and U.S. Patent Publ. Nos. 20010014448, 20030148360, and 20090042742 (each of which is incorporated herein in its entirety by reference thereto).

In one embodiment, the chemical linking moiety has the formula A-X—B in which A represents a photochemically reactive group capable of bonding covalently to a solid surface; B represents a different reactive group capable desirably in response to specific activation to which group A is unresponsive, of forming a covalent bond to a biocompatible agent and X represents a relatively inert, noninterfering skeletal moiety joining groups "A", and "B", that is resistant to cleavage in aqueous physiological fluid. The physiological fluid referred to is such fluid with which X will come in contact (e.g., blood, interstitial fluid, etc.). In a method of the invention group "A" of the linking moiety is covalently bound to the solid surface, with a sufficient population density to enable the molecules of the biocompatible agent to effectively shield the solid surface when the molecules are covalently bound to group "B" to provide a biocompatible effective surface. A biocompatible device of this invention includes a solid surface to which molecules of a biocompatible agent have been bound via the chemical-linking moiety as follows: solid surface-A residue-X—B residue-molecules of a biocompatible agent.

In one embodiment, the molecules of the biocompatible agent are selectively bound to the solid surface with a sufficient population density to provide a biocompatible effective surface using a chemically linking moiety that has the formula:

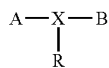

in which R represents a selector group that is a member of a specific bonding pair and that is reactive to form a bond with a receptor forming the other member of the specific binding pair and carried by a selected biocompatible agent and A, and B represent the groups described above as A and B. X represents a relatively inert, non-interfering skeletal radical joining groups "A", "B" and "R" and sterically enabling group "B" to separate from group "R" by at least about 10 Å.

Groups "B" and "R" are preferably sterically distinct groups; that is, they may, during the course of thermal vibration and rotation separate by a distance of at least about 10 Å. Group R, a "selector" group, representing a member of a specific binding pair, commonly forms a bond, usually non-covalent, with the biocompatible agent at an epitopic or other binding site of the latter (which site typifies a "receptor" herein). The group "B", which upon activation can covalently bond to the biocompatible agent, may be sterically spaced from the group "R", thereby enabling the covalent bond to be formed at a site spaced from the receptor site. In turn, the selector receptor bond may be disassociated from the receptor site through breakage of a fragile bond between the selector group and the chemical linking moiety followed by removal of the selector by, e.g., dialysis, environmental changes (pH, ionic strength, temperature, solvent polarity, etc.) or through spontaneous catalytic modification of the selector group (as when the biocompatible agent is an enzyme), etc. The receptor thus is reactivated to permit subsequent reaction with members of the specific binding pair.

As referred to herein, "specific binding pair" refers to pairs of substances having a specific binding affinity for one another. Such substances include antigens and their antibodies, haptens and their antibodies, enzymes and their binding partners (including cofactors, inhibitors and chemical moieties whose reaction the enzymes promote), hormones and their receptors, specific carbohydrate groups and lectins, vitamins and their receptors, antibiotics and their antibodies and naturally occurring binding proteins, etc. The concept of employing specific binding pairs in analytical chemistry is well known and requires little further explanation. Reference is made to Adams, U.S. Pat. No. 4,039,652, Maggio, et al, U.S. Pat. No. 4,233,402 and Murray, et al, U.S. Pat. No. 4,307,071, the teachings of which are incorporated herein by reference.

In certain embodiments, X is preferably a $C_1$-$C_{10}$ alkyl group such as polymethylene, a carbohydrate such as polymethylol, a polyoxyethylene, such as polyethylene glycol or a polypeptide such as polylysine.

The reactive group B is preferably a group that upon suitable activation covalently bonds to proteinaceous or other biocompatible agents. Such groups are typified by thermochemical groups and photochemical groups, as described and exemplified in Guire, U.S. Pat. No. 3,959,078, the teachings of which are incorporated herein by reference.

The photochemically reactive groups (A) (the covalent bonding of which is activated by actinic radiation) may be typified by aryl, alkyl and acyl azides, oxazidines, isocyanates (nitrene generators), alkyl and 2 ketodiazo derivatives and diazirines (carbene generators), aromatic ketones (triplet oxygen generators), aromatic diazonium derivatives and numerous classes of carbonium ion and radical generators. Reference is made to Frederick J. Darfler and Andrew M. Tometsko, chapter 2 of Chemistry and Biochemistry of Amino Acids, Peptides and Proteins (Boris Weinstein, ed) vol. 5, Marcel Dekker, Inc. New York, 1978, for further description of photochemically reactive groups. Azidonitrophenyls, fluoroazido nitrobenzenes, and aromatic ketones form a preferred group due to their stability to chemical reaction conditions in the dark and their susceptibility to activation by light of wave lengths harmless to most biomaterials, to form short-lived reactive intermediates capable of forming covalent bonds in useful yield with most sites on the biomaterial.

Nitrophenylazide derivatives (shown as including the X group) appropriate for use as photochemically reactive groups for the most part can be derived from fluoro-2-nitro-4-azidobenzene, and include 4-azido-2-nitrophenyl(ANP)-4-aminobutyryl, ANP-6-aminocaproyl, ANP-11-aminoundecanoyl, ANP-glycyl, ANP-aminopropyl, ANP-mercaptoethylamino, ANP-diaminohexyl, ANP-diaminopropyl, and ANP-polyethylene glycol. ANP-6-aminocaproyl, ANP-11-aminoundecanoyl, and ANP-polyethylene glycol are preferred. Aromatic ketones preferred for use as photochemically reactive groups include benzylbenzoyl and nitrobenzylbenzoyl.

Thermochemical reactive groups (that are activated by heat energy) are typified by and include nitrophenylhalides, alkylamino, alkylcarboxyl, alkylthiol, alkylaldehyde, alkylmethylimidate, alkylisocyanate, alkylisothiocyanate and alkylhalide groups.

Groups appropriate for use as thermochemically reactive groups include carboxyl groups, hydroxyl groups, primary amino groups, thiol groups, maleimides and halide groups. N-oxysuccinimide carboxylic esters of such groups as 6-amino hexanoic acid and amino undecanoic acid, alkylthiol groups such as mercaptosuccinic anhydride and beta-mercaptopropionic acid, homocysteinethiolactones, and polyetheylene glycol derivatives are preferred.

Other linking agents can also be used in the embodiments of the present disclosure, such as those disclosed in U.S. Pat. No. 6,077,698, which is incorporated herein by reference. For example, a chemical linking agent comprising a di- or higher functional photoactivatable charged compound can be used. The linking agent preferably provides at least one group that is charged under the conditions of use in order to provide improved water solubility. The linking agent may further provide two or more photoactivatable groups in order to allow the agent to be used as a cross-linking agent in aqueous systems. In preferred embodiments, the charge is provided by the inclusion of one or more quaternary ammonium radicals, and the photoreactive groups are provided by two or more radicals of an aryl ketone such as benzophenone.

The thromboresistant agent may carry one or more latent reactive groups covalently bonded to them. The latent reactive groups are groups which respond to specific applied external stimuli to undergo active specie generation with resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups as described are generally well known.

The azides constitute a preferred class of latent reactive groups and include arylazides, such as those disclosed in U.S. Pat. No. 5,002,582, which is incorporated by reference herein, for example phenyl azide and particularly 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, and phosphoryl azides such as diphenyl phosphoryl azide and diethyl phosphoryl azide. Diazo compounds constitute another class of latent reactive groups and include diazoalkanes (—$CHN_2$) such as diazomethane and diphenyldiazomethane, diazoketones such as diazoacetophenone and 1-trifluoromethyl-1-diazo-2-pentanone, such as t-butyl diazoacetate and phenyl diazoacetates, and beta-ketone-alpha-diazoacetates such as t butyl alpha diazoacetoacetate. Other latent reactive groups include the aliphatic azo compounds such as azobisisobutyronitrile, the diazirines such as 3-trifluoromethyl-3-phenyldiazirine, the ketenes (—CH═C═O) such as ketene and diphenylketene and photoactivatable ketones such as benzophenone and acetophenone. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate. Upon activation of the latent reactive groups to cause covalent bond formation to the surfaces to which polymer molecules are to be attached, the polymer molecules are covalently attached to the surfaces by means of residues of the latent reactive groups. Exemplary latent reactive groups are recited in U.S. Pat. No. 5,002,582 incorporated herein by reference.

The polymers and oligomers used may have one or more latent reactive groups. In certain embodiments, the polymers have at least one latent reactive group per molecule with the ratio of reactive groups extended polymer length, in Angstroms, ranging from about 1/10 to about 1/700 and preferably from about 1/50 to 1/400. As will be noted from the foregoing description, photoreactive latent reactive groups are for the most part aromatic and hence generally are hydrophobic rather than hydrophilic in nature.

The latent reactive groups and the polymer molecules to which they are bonded may have substantially different solvophilic properties. For example, the latent reactive groups may be relatively hydrophobic, whereas the polymer molecules may be relatively hydrophilic; when solution of the molecules is contacted with a relatively hydrophobic surface, it is believed that the latent reactive groups, being hydrophobic, tend to orient nearer the surface so as to improve bonding efficiency when the latent reactive groups are activated. The preferred latent reactive groups are benzophenones, acetophenones, and aryl azides.

The loading density of polymers upon a surface may be improved by a process in which a latent reactive molecule (a molecule having a latent reactive group) is first brought into close association (as by means of a solvent solution) to a surface, and thereafter the polymer to be bonded to the surface is brought into contact with and is covalently bonded to the latent reactive molecule, as to a reactive group different from the latent reactive group. Thereafter, the latent reactive groups may be activated to cause them to covalently bond to the surface to thereby link the polymers to the surface.

In other embodiments, polymer chains may be provided upon a surface or other substrate by first covalently bonding to the substrate through a latent reactive group a monomer, oligomer or other reactive chemical unit. To the thus bonded reactive units are covalently bonded monomers or oligomers in a polymerization reaction or polymers via covalent bonding (grafting) of the reactive units onto the polymer chains.

The reactive chemical units of the invention carry covalently bonded thereto latent reactive groups as described herein for covalent attachment to a non pretreated surface or other substrate. These molecules are characterized as having reactive groups capable of covalent bonding to polymer molecules of a polymer having the desired characteristics, or of entering into a polymerization reaction with added monomers or oligomers to produce polymer chains having the desired characteristics. Reactive chemical molecules capable of covalently bonding to polymer molecules include not only monomers and oligomers of various types but also molecules having such functional groups as carboxyl, hydroxyl, amino, and N-oxysuccinimide, such groups being reactive with reactive groups carried by the polymer chain to bond to the chain. The reactive chemical molecules are preferably monomers or oligomers and most preferably are ethylenically unsaturated monomers capable of entering into an addition polymerization reaction with other ethylenically unsaturated monomers. Particularly preferred are the acrylate and methacrylate monomers which are the esterification products of acrylic or methacrylic acid and hydroxy-functional latent reactive groups. Examples of such molecules include 4-benzoylbenzoyl-lysyl-acrylate.

Utilizing reactive chemical units bearing latent reactive groups, one may first coat a surface or other substrate with a solvent solution of such molecules. Upon removal of solvent, the application of an appropriate external stimulus such as U.V. light will cause the molecules to covalently bond, through the latent reactive groups, to the substrate. The substrate may then be appropriately contacted with a solution containing the desired polymer, monomer or oligomer molecules to cause bonding to these molecules. For example, if the reactive chemical unit molecule is carboxyl functional, it may be reactive with, and covalently bonded to, an appropriate hydroxyl-functional polymer such as dihydroxy polyethylene glycol. If the reactive chemical molecule is a monomer or oligomer, e.g., a methacrylate monomer, the substrate to which the molecule is covalently bonded may be contacted with a solution of addition-polymerizable monomers such as hydroxyethyl methacrylate and a free-radical addition polymerization initiator such as dibenzoyl peroxide under addition polymerization conditions to result in the growth of polymer chains from the monomer molecules bound covalently to the substrate. Once the desired polymerization has occurred, the substrate may be washed to remove residual monomer, solvent and non bound polymer that was formed.

In other embodiments the thromboresistant coating can adhere better by surface modification of the medical device by adsorbing a layer of a polyamine having a high average molecular weight on to the surface. The polyamine is stabilised by cross-linking with crotonaldehyde, which is a monoaldehyde having a C—C double bond in conjugation with the aldehyde function. Thereafter one or more alternating layers of an anionic polysaccharide and the cross-linked polyamine, followed by a final layer of the said polyamine, not cross-linked, may be adsorbed onto the first layer of cross-linked polyamine, whereby a surface modification carrying free primary amino groups is achieved.

In certain embodiments, the thromboresistant coating is made by bringing the substrate into contact with an aqueous solution of the polyamine at pH 8-10, for example pH 9. The concentration of the initial polyamine solution will range from 1-10% by weight, especially 5% by weight, 1 ml of which may be diluted to a final volume of 500-2000 ml, especially 1000 ml. This final solution may also comprise from 100-1000 µl especially 340 µl crotonaldehyde. Alternatively the substrate will be treated first with a solution of polyamine of said concentration and pH, and then with a solution of the crotonaldehyde of the said concentration and pH. The temperature is not critical, so it is preferred for the treatment to be at room temperature.

After rinsing with water, the substrate is treated with a solution of an anionic polysaccharide, containing from about 10 to about 500 mg, preferably about 100 mg of the polysaccharide in a volume of 1000 ml. This step is executed at a temperature in the range of 40°-70° C., preferably about 55° C. and pH 1-5, preferably about pH 3.

After another rinsing with water, these first steps may be repeated one or several times and finally, after having adsorbed a layer of polysaccharide, the substrate may be treated with a polyamine solution having a concentration 1-20 times, preferably 10 times, that mentioned above, at the said temperature and pH. The polyamine will preferably be a polymeric aliphatic amine, especially polyethylene imine having a high average molecular weight, but any polyamine having a high average molecular weight and carrying free primary amino groups may be used. The anionic polysaccharide will preferably be a sulfated polysaccharide. The aminated surface may optionally be further stabilized by reduction with a suitable reducing agent such as sodium cyanoborohydride. The modified surface according to present invention has free primary amino groups by which chemical entities may be bound either ionically or covalently. Also aldehyde containing chemical entities may be bound by formation of Schiffs bases, eventually followed by a stabilization reaction such as a reduction to convert the Schiffs bases to secondary amines. Further examples are disclosed in U.S. Pat. No. 5,049,403 which is hereby incorporated by reference in its entirety.

In certain embodiments, to provide a thromboresistant coating to the medical device, a composition is prepared to include a solvent, a combination of complementary polymers dissolved in the solvent, and the bioactive agent or agents dispersed in the polymer/solvent mixture. The solvent is preferably one in which the polymers form a true solution. The pharmaceutical agent itself may either be soluble in the solvent or form a dispersion throughout the solvent.

Due to the properties of materials frequently used on the outer surface of sensors, sensors can be difficult to coat with conventional anticoagulants, or anti-thrombogenics, e.g., heparin, to obtain a suitable anticoagulant coating, which is sufficiently stable, long-lasting, and active for preferred intravascular applications, and yet is sufficiently invisible to analytes of interest and non-interfering with the sensor chemistry to allow reliable and sufficiently long-lasting operation. Various issues can arise relating to the suitability of a particular coating including, for example, stability of the coating during manufacturing and handling of the sensor, resistance of the coating to removals during use, such as by solubilization, reaction, etc., resistance to diffusion through the coating of analytes of interest, and interaction between species in the coating and the sensor technology, whether by hydrolysis of detectable species from the coating or by other means.

Coating materials comprising heparin are preferred, but other polysaccharide and biologically derived materials and analogs can be utilized as well, either with heparin or in place of heparin. Preferred methods of applying the coating include application of a heparin-quaternary ammonium complex in isopropanol to a sensor wetted with water or water/surfactant under vacuum, but other suitable methods of applying a coating can also be successfully employed, such as application of a heparin-quaternary ammonium complex from combinations of solvents, such as non-polar solvents and polar solvents; sequential application of quaternary ammonium compound and heparin, such as to form a heparin-quaternary ammonium complex in-situ; covalently bonding heparin molecules to the surface of the sensor, including methods for attaching individual ends of heparin molecules to the surface such as described by Carmeda AB (Upplands Vasby, Sweden); and application of cross-linked forms of heparin or heparin with other compounds.

In certain embodiments, a coating of heparin or a heparin containing material can be applied to at least a portion of the sensor surface to limit or prevent thrombus formation. However, in some cases, application of such a coating can be difficult due to problems of adhesion where the coating will not properly adhere to the surface initially or will tend to detach or dissolve from the surface upon use. Instances where the coating detaches upon use can be particularly problematic due to the possibility of particulate impurities being released into the bloodstream and the possibility that these can result in plugging of small blood vessels. In addition, detachment or dissolution of heparin coating material can result in therapeutic or sub-therapeutic dosing of the patient with an anticoagulant material. Such adhesion problems can be particularly pronounced when applied to certain types of materials, especially plastics such as polyolefins, fluoropolymers, polycarbonate, and polysulfone. For example, polyolefins and fluoropolymers in particular are especially difficult to adhere materials to, as evidenced by the difficulty and limited strength that is typically achieved when these plastics are glued.

The present inventors have found that surprisingly a coating comprising heparin and benzalkonium can be effectively applied and will maintain an acceptably stable and active coating over polymeric surfaces of analyte sensors disclosed herein, including polymeric surfaces such as polyolefins, fluoropolymers, polycarbonate and polysulfone, porous polymeric surfaces, and porous polymeric surfaces on sensors incorporating immobilizing polymeric matrices, while still maintaining acceptable functionality of the analyte sensor. In certain embodiments, the porous surfaces capable of maintaining an acceptably stable and active coating comprising heparin and benzalkonium are more specifically described as microporous, nanoporous, or mesoporous.

In preferred embodiments, the coating comprising heparin and benzalkonium may include pharmaceutical grade heparin, such as heparin sodium or heparin calcium as described in the U.S. Pharmacopeia, revised Jun. 18, 2008, however, other grades and forms of heparin can be utilized in various applications, including instances where pharmaceutical regulations do not apply. Preferred grades of heparin can have an average molecular weight of about 12 to about 15 kDa, however, individual strands can have molecular weights as high as about 40 kDa or 50 kDA or even higher, and as low as about 5 kDa or 3 kDa or even lower. In other embodiments, heparin with average molecular weights higher or lower than about 12 to about 15 kDa can be successfully utilized, such as those as high as about 20 or 30 kDa or as low as about 7 or 10 kDa.

In some preferred embodiments, the coating comprising heparin and benzalkonium may include molecules of benzalkonium chloride having alkyl groups of about 1 to about 5 carbons for two of the R-groups and an alkyl group of about six to about 22 carbons for the third R-group, either as a single pure compound or as a combination of compounds with differing R-groups. In some embodiments, grades of benzalkonium chloride include those having compounds and mixtures of compounds having primarily two methyl groups and an alkyl group of about six to about 22 carbons, or more preferably two methyl groups and an alkyl group of about 10 to about 18 carbons as the R-groups.

In certain embodiments, other ammonium complexes can be used, e.g., particular alkylbenzyl dimethyl ammonium cationic salts, which can be used in high loading concentrations with heparin to form coatings, as disclosed in U.S. Pat. No. 5,047,020 to Hsu; incorporated herein in its entirety by reference. Hsu found that commercially available benzalkonium chloride may comprise a mixture of alkylbenzyldimethylammonium chloride of the general formula, $[C_6H_5CH_2N(CH_3)_2R]Cl$, in which R represents a mixture of alkyls, including all or some of the groups comprising C8 and greater, with C12, C14 and C16 comprising the major portion. Generally, the composition breaks down to more than 20% C14, more than 40%, C12 and a less than 30% mixture of C8, C10 and C16. In contrast, Hsu found that preferred heparin/quaternary ammonium complexes have at least about 50 weight percent of the organic cationic salt, and preferably from 60 to 70 weight percent. Hsu found that optimum results were achieved with complexes consisting of cetalkonium heparin and/or stearylkonium heparin and mixtures thereof. Indeed, Hsu teaches that coatings for medical devices consisting of complexes of cetalkonium heparin and/or stearylkonium heparin and mixtures thereof, exhibit "vastly superior hydrophobicity and surface adhesion over the presently and most commonly used complexes of heparin and benzalkonium chloride." Accordingly, in another aspect of the invention, other heparin/quaternary ammonium complexes besides those comprising benzalkonium, like those disclosed by Hsu, may be used to coat and render thromboresistant the glucose sensors disclosed herein.

Surface Coating Agents

Various compounds can be useful as coating agents for the thromboresistant coating of the medical device, for example those disclosed in U.S. Pat. Nos. 6,278,018, 6,603,040, 6,924,390, 7,138,541, which are all incorporated herein by reference. In one aspect, the present invention provides a compound comprising a nonpolymeric core molecule comprising an aromatic group, the core molecule having attached thereto, either directly or indirectly, one or more substituents comprising negatively charged groups, and two or more photoreactive species, wherein the photoreactive species are provided as independent photoreactive groups. The first and second photoreactive species of the present coating agent can, independently, be identical or different.

In certain embodiments the core is provided as the residue of a polyhydroxy benzene starting material (e.g., formed as a derivative of hydroquinone, catechol, or resorcinol), in which the hydroxy groups have been reacted to form an ether (or ether carbonyl) linkage to a corresponding plurality of photogroups. In one embodiment, a coating agent of this invention further comprises one or more optional spacers that serve to attach a core molecule to corresponding photoreactive species, the spacer being selected from radicals with the general formula: wherein n is a number greater or equal to 1 and less than about 5, and m is a number greater or equal to 1 and less than about 4.

In another embodiment, such coating agents are selected from the group 4,5-bis(4-benzoylphenylmethyleneoxy)benzene-1,3-disulfonic acid di(potassium and/or sodium) salt, 2,5-bis(4-benzoylphenylmethyleneoxy)benzene-1,4-disulfonic acid di(potassium and/or sodium) salt, 2,5-bis(4-benzoylphenylmethyleneoxy)benzene-1-sulfonic acid monopotassium and/or monosodium salt.

Suitable core molecules of the present invention include nonpolymeric radicals having a low molecular weight (e.g., 100-1000 MW). Suitable core molecules provide an improved combination of such properties as coating density, structural stability, ease of manufacture, and cost. Further, core molecules can be provided with water soluble regions, biodegradable regions, hydrophobic regions, as well as polymerizable regions. Examples of suitable core molecules include cyclic hydrocarbons, such as benzene and derivatives thereof.

The type and number of charged groups in a preferred coating agent are sufficient to provide the agent with a water solubility (at room temperature and optimal pH) of at least about 0.1 mg/ml, and preferably at least about 0.5 mg/ml, and more preferably at least about 1 mg/ml. Given the nature of the surface coating process, coating agent solubility levels of at least about 0.1 mg/ml are generally adequate for providing useful coatings of target molecules (e.g., polymer layers) on surfaces.

The coating agent can thus be contrasted with many coating agents in the art, which are typically considered to be insoluble in water (e.g., having a comparable water solubility in the range of about 0.1 mg/ml or less, and more often about 0.01 mg/ml or less). For this reason, conventional coating agents are typically provided and used in solvent systems in which water is either absent or is provided as a minor (e.g., less than about 50% by volume) component.

Examples of suitable charged groups include salts of organic acids (e.g., sulfonate, phosphonate, and carboxylate groups), as well as combinations thereof. A preferred charged group for use in preparing coating agents of the present invention is a sulfonic acid salt, e.g., derivatives of $SO_3^-$ in which the counterion is provided by the salts of Group I alkaline metals (Na, K, Li ions) to provide a suitable positively charged species.

The use of photoreactive species in the form of photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultravieolet light-induced exitation of the benzophenome group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

Coating Methodology

The coating processes disclosed herein include: 1) direct coating of the heparin complex by straight application, as in the case of dip coating, as well as 2) indirect coating, as in the case of sequential applications of a quarternary ammonium salt plus surfactant and the ionic heparin. Suitable methods for applying a coating comprising heparin and benzalkonium may include multistep layering techniques as well as single step application of heparin complexes. In other embodiments, pretreatment methods are used, such as soaking the sensors in sodium heparin solutions.

In the event that it is desired to apply the thromboresistant coating to surfaces that are inert to certain polymeric materials, adhesion can be facilitated by chemically treating the surfaces in order to provide hydroxyl groups on or near the surface thereof. Exemplary chemical surface treatments in this regard include such known procedures as chemical etching, surfactant adsorption, coextrusion, plasma discharge, surface oxidation or reduction, radiation activation and oxidation, and surface grafting with materials such as polyvinyl alcohol, poly(2-hydroxyethyl methacrylate) and the like. Bulk modifications of the substrate surface can also be accomplished in order to provide active hydrogens. Examples of conventional modifications of this type include blending with polymers having active hydrogens, partial degradation of polymers, end group modification, monomer functionalization, oxidation, reduction, copolymerization, and the like.

In certain embodiments, a three-dimensional highly crosslinked matrix containing aminosilanes is formed on the medical device surface. The aminosilane is cured, crosslinked or polymerized in place on the surface to be rendered thromboresistant. This is carried out in a manner such that a three-dimensional matrix is formed. The matrix can be either an aminosilane homopolymer or a copolymer, including a graft copolymer, of an aminosilane with another silane that is not an aminosilane. Representative aminosilanes include 3-aminopropyltrimethoxysilane, 3-aminopropyltriethoxysilane, 2-aminoundecyltrimethoxysilane, aminophenyltrimethoxysilane, N-(2-aminoethyl-3-aminopropyl)trimethoxysilane, and trimethoxysilylpropyldiethylenetriamine.

Aminosilanes of this type can be used alone in order to form a homopolymer matrix. For example, certain aminosilanes are trifunctional and provide a highly crosslinked matrix. The hydrophilicity can be reduced, when desired, by combining the hydrophilic aminosilane with a less hydrophilic silane that is not an aminosilane. In one embodiment, a matrix that is a copolymer of one of these aminosilanes with another silane molecule that is not an aminosilane and that is less hydrophilic than an aminosilane in order to thereby adjust the hydrophilicity of the matrix. Other methods and coating agents are also known in the art, including U.S. Pat. Nos. 5,053,048, 4,973,493, 5,049,403, all of which are incorporated by reference herein.

In preferred embodiments, a coating comprising heparin and benzalkonium is applied by first wetting the sensor surface with water or a combination of water and surfactant. Preferred surfactants include anionic surfactants, however other surfactants such as cationic surfactants or non-ionic surfactants may also be successfully employed in some embodiments. In particular, suitable surfactants include sodium laurel sulfate, sodium dodecyl sulfate, ammonium lauryl sulfate, sodium laureth sulfate. The wetted sensor is then treated with an alcoholic solution of heparin-quaternary ammonium complex. In certain embodiments, the alcoholic solution comprises isopropanol, however other alcohol based solutions may be used as well, depending on the embodiment. Preferred solutions of isopropanol may include about 1 to about 99% (wt.) of heparin-benzalkonium complex in isopropanol, including 5%, 10%, 25%, 50%, 75%, 90%, and 95% (and also including ranges of weight percentages bordered on each end by these recited weight percentages). One preferred solution of heparin-benzalkonium in isopropanol is manufactured by Celsus Laboratories, Inc. 12150 Best Place, Cincinnati Ohio 45241, under product number BY-3189 (described as Benzalkonium heparin solution in isopropyl alcohol, 887 U/mL). The wetted sensor can be dipped in the heparin-benzalkonium solution, or it can be sprayed onto the surface of the sensor or applied by another suitable technique. The sensor with coating solution applied is then dried. Additional coating material, such as to improve consistency of a coating or to thicken a coating, can be applied by dipping, spraying or other suitable means. When material is applied, preferred methods include those where the sensor is exposed to the heparin-benzalkonium solution for only a limited time, such as less than one minute, or less than about 30 seconds or about 10 seconds or even about 1 or 2 seconds, such as by dipping the sensor into the solution for only about a second (and also including time intervals bordered on the high end and the low end by the recited durations such as dipping the sensor into the solution for between 10 and 30 seconds). In some embodiments, short time intervals can prevent undesirable results, such as excessive solubilization of material from the sensor surface or excessive dehydration of the sensor. However, in some embodiments, longer time periods can successfully be utilized by, for example, increasing the concentration of heparin-benzalkonium concentration of the solution or by supplementing the solution with additional benzalkonium material or heparin material, or by adjusting the pH, or ionic strength of the solution. In some embodiments, during the coating process, the sensor can be rehydrated as needed or desired by application of water or a combination of water and surfactant and/or solvent.

However, other methods of applying a coating comprising heparin and benzalkonium can also be successfully employed. Suitable multistep layering techniques include those techniques where an heparin and benzalkonium are applied by a process comprising application of a suitable form and grade of benzalkonium chloride followed by application of a suitable form and grade of heparin. Any suitable solvent or combinations of solvents can be used for heparin, such as water or aqueous alcohol, and for benzalkonium chloride, such as nonpolar organic solvents (for example, toluene, petroleum ether, etc.). Preferred heparin solutions include those comprising heparin in a weight percentage of about 0.05%, 1%, 5%, 10%, 25%, 50%, 75%, 90%, and 95% (and also including ranges of weight percentages bordered on each end by these recited weight percentages). In certain such embodiments, a preferred heparin solution comprises a weight percent of heparin between about 0.05% to about 1%. Preferred benzalkonium chloride solutions include those comprising benzalkonium in a weight percentage of about 0.05%, 1%, 5%, 10%, 20%, 25%, 50%, 75%, 90%, and 95%

(and also including ranges of weight percentages bordered on each end by these recited weight percentages). In certain such embodiments, a preferred benzalkonium chloride solution comprises a weight percent of benzalkonium chloride between about 1.0% to about 20%.

Other suitable coating techniques are described, for example, in U.S. Pat. No. 3,846,353, to Grotta, and U.S. Pat. No. 5,047,020, to Hsu, incorporated by reference herein in their entireties.

Single step application of heparin complexes can comprise applying a solution comprising heparin and benzalkonium of a suitable grade and form to the sensor, such as is described in U.S. Pat. No. 5,047,020, to Hsu. In certain embodiments, the solution may include benzalkonium chloride. Suitable solvents for the heparin and benzalkonium include those comprising polar organic solvents, alone or as mixtures, such as alcohols (e.g. isopropanol), halogenated solvents (e.g. trifluoro-trichloro ethane), etc. In some embodiments, the solution to be applied to the polymeric surface may include heparin and benzalkonium in a combined weight percentage of 0.1%, 1%, 5%, 10%, 25%, 50%, 75%, or about 90% of the total weight of the solution (also including ranges of weight percentages bordered on each end by these recited weight percentages). In certain such embodiments, a solution may contain between about 0.1% to about 75% heparin/benzalkonium by weight. In some embodiments, successive layers of heparin/benzalkonium complex can be applied to the surface of the sensor, for example, to build up a coating having a desired thickness and/or durability.

In certain embodiments, the distal portion of a pre-wetted sensor is dipped in a solution comprising heparin and benzalkonium in isopropanol, preferably for about 0.1 to about 30 seconds, and more preferably for about 1 to about 10 seconds, and even more preferably for about 1 second. In certain embodiments, the dipped sensor is subsequently air dried, preferably for at least about 10 seconds, and more preferably for about 0.5 minutes to about 10 minutes, and even more preferably for about 1 minute. The heparin/benzalkonium coating and drying steps are repeated in accordance with various embodiments, preferably from about 1 to about 20 times, or more preferably from about 2 to about 10 times, or even more preferably from about 3 to about 8 times, and even more preferably still from about 4 to about 6 times.

In certain embodiments, a sustained release of heparin from the sensor surface into the surrounding vessel is achieved by soaking the sensor. In one embodiment, the sensor, which optionally contains a hydrogel underneath the optional microporous membrane, is soaked in a solution of heparin for infusion of heparin into the swollen hydrogel. In one embodiment, an aqueous solution of at least about 10% sodium heparin is used. In a more preferred embodiment, an aqueous solution of at least about 20% sodium heparin is used. In a most preferred embodiment, an aqueous solution of at least about 30% sodium heparin is used. In other embodiments, other organic solvents and other forms of heparin may be used. In one embodiment, the sodium heparin solution is in phosphate buffered saline of about pH 5. After soaking for enough time to saturate the hydrogel, the sensor is removed from the solution and allowed to dry. In one embodiment, the sensor is soaked for at least about 1 hour. In a preferred embodiment, the sensor is soaked for about 2 hours. In one embodiment, the sensor is soaked for at least about 3 hour. When the sensor is then deployed in-vivo, the hydrogel re-swells in the bloodstream thus releasing the heparin gradually over time.

Additional steps can be utilized as necessary, such as, for example, cleaning the surface of the sensor with suitable agents such as solvents, surfactants, etc. and/or drying the coating, such as with a gas stream, or with heat, or with a heated gas stream, or with one or more dehydrating agents. In some embodiments, it is desirable to package the sensor as soon as possible after coating, since in some embodiments, after coating, the surface of the sensor may be somewhat tacky, and it may tend to pick up particulate matter.

Other methods of applying a heparin-based coating to the sensor includes covalently bonding heparin, or a heparin derivative, to the surface of the sensor or to an intermediate material applied to the surface of the sensor. Suitable techniques include those that covalently bond the end of a heparin molecule to the surface of the sensor or an intermediate, such as the techniques utilized by Carmeda AB (Upplands Vasby, Sweden). Other suitable methods also include those utilizing photoimmobilization to attach heparin, or a heparin derivative to the surface of a sensor or an intermediate material applied to the surface of the sensor, such as are described herein and by Surmodics (Eden Prairie, Minn.), as well as those depositing heparin complexes with polar and nonpolar solvents, such as are described in U.S. Pat. No. 6,833,253 to Roorda, et al.

WORKING EXAMPLES

Example 1

Application of Thromboresistant Coating

An optical glucose sensor as described above (see e.g., FIGS. 1-4) was prepared for coating with benzalkonium/heparin by immersing the portion of the sensor to be coated in a pH 3 phosphate buffered saline solution (although it is feasible to use many types of aqueous buffer solutions or even just water).

A coating solution of 1.5% (by weight) benzalkonium heparin in isopropanol (distributed by Celsus Laboratories, Inc. 12150 Best Place, Cincinnati Ohio 45241 as Benzalkonium heparin solution in isopropyl alcohol, 887 U/mL, Product Number BY-3189) was added to a test tube. After equilibrating in the buffered saline solution, the distal end portion of the sensing end of the sensor was immersed in the benzalkonium heparin solution and immediately removed (with the time of immersion in the benzalkonium heparin solution being approximately one second). The wet sensor was allowed to air dry for approximately 1 minute, resulting in a coating of benzalkonium heparin on the sensor surface.

Immersion of the sensor in the benzalkonium/heparin solution followed by air drying was repeated 4 times to build up additional coating material on the surface of the sensor.

Example 2

Preparation of Sensor Blank

A sensor blank was prepared from a polyethylene microporous membrane (of 0.017 inch outside diameter) surrounding a poly(methyl methacrylate) optical fiber (of 0.010 inch diameter). The polyethylene microporous membrane was obtained from Biogeneral 9925 Mesa Rim Road, San Diego Calif. 92121-2911). The distal end of the sensor blank (the end to be coated) is heat welded to a rounded polyethylene plug. The other end is sealed with a silicone backfill. The distal end was then immersed in the buffered saline solution of Example 1 for about 18 hours (although a shorter time interval would also have been suitable). Finally, the distal end of the sensor blank was immersed in the coating solution of Example 1 and subsequently air dried as in Example 1. The steps of immersing in the coating solution and air drying were repeated four times.

Example 3

Comparison of Coated Sensor and Coated Sensor Blank

Coated sensors and coated sensor blanks, prepared as described in Examples 1 and 2, each having five dip coats of heparin/benzalkonium applied, were subjected to handling tests as follows.

Sensors consisted of a 1.3-inch long hollow, microporous HDPE membrane (0.017 inches O.D., Biogeneral 9925 Mesa Rim Road, San Diego Calif. 92121-2911, this is a custom part) butt-welded to a 1.0-inch long, smooth (nonporous) HDPE tube. The microporous end was heat-welded to a rounded polyethylene plug. Inside of the hollow assembly was threaded a 0.010 inch PMMA optical fiber The smooth HDPE end was filled with silicone backfill up to, but not including, the microporous membrane. The area between the PMMA optical fiber and the hollow microporous membrane was filled with a dimethyl acrylamide gel which also contained covalently-bound fluorescent dye and quencher. The sensor was prepared for application of the coating comprising heparin and benzalkonium by immersing the distal ("sensor") end in an aqueous solution of phosphate buffered saline as described in Example 1 for about 18 hours (although this amount of time may not be necessary). The sensor was then immersed in the heparin/benzalkonium solution and air dried as described in Example 1. The immersion and drying steps were repeated 4 times.

After repeated immersions in the coating solution and drying, the sensors and sensor blanks were prepared for the handling tests by staining with toluidine blue. Specifically, the sensors and sensor blanks were pulled through the silicone rubber seal, and then dipped in a 0.04% solution of toluidine blue in water for 1 minute, rinsed with water and allowed to air dry for 30 minutes.

Figure 7A:
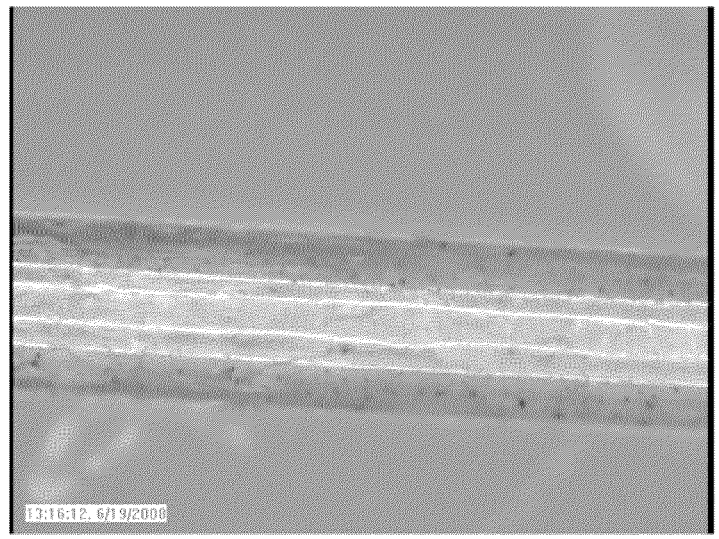
FIG. 7A illustrates the adhesion of a coating of heparin benzalkonium to a microporous membrane section of a sensor.
Figure 7B:
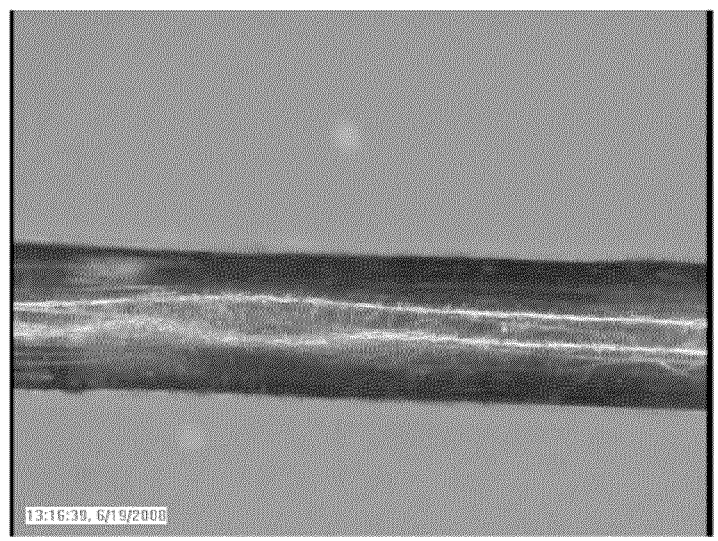
FIG. 7B illustrates the adhesion of a coating of heparin benzalkonium to a nonporous precursor section of a sensor.

Toluidine blue stains heparin a purple color, and so a darker purple color tends to indicate a higher concentration of heparin than a lighter purple color or no purple color at all. Thus, in order to assess the durability of the heparin coating, the stained sensors and sensor blanks were subjected to the following handling tests and subsequently visually examined under 20× magnification to discern voids and thinness in the heparin coating indicated by the lightening of the toluidine stain. The results are described below as well.
Storage in Phosphate Buffered Saline Solution Sensors were soaked in pH 7.4 phosphate buffered saline for up to 48 hours at 37 C. Microporous membrane sections were observed to retain an even purple color even after 48 hours. The stain on nonporous polyethylene sections became lighter and less even after as little as 2 hours.
Storage in Sensor Housing Assembly A coated sensor was placed into a sensor housing assembly, consisting of a polyurethane tubing and sealed with a parylene-coated silicone rubber seal. The housing assembly was filled with pH 7.4 phosphate buffered saline and the sensor was soaked in the housing for 1 hour at room temperature. Afterwards, the nonporous polyethylene section displayed (under magnification) clear signs of damage to the heparin coating, with apparent scrapes and voids in the purple stain. In contrast, the microporous membrane section looked unaffected, with a consistent and smooth purple stain. Abrasion: A sensor was soaked in pH 7.4 phosphate buffered saline for 1 hour at room temperature, then rubbed vigorously with a wet nitrile glove for one minute. It was then stained with toluidine blue. Under magnification, the nonporous polyethylene section was almost completely devoid of purple stain, indicating a total loss of the heparin coating. The microporous membrane section looked to be diminished and somewhat patchy, although there was still a strong purple color along the entire length. It should be noted that the handling in this portion of the test was very extreme.
Sonication with Isopropanol One sensor was sonicated three times in successive vials of 25 mLs isopropanol for 5 minutes each. It was then stained with toluidine blue. Under magnification, the nonporous precursor polyethylene section was almost completely devoid of purple stain, indicating total loss of the heparin coating, as shown in FIG. 7A. The microporous membrane section still maintained a strong, even purple color, indicating that a consistent heparin coating remained, as shown in FIG. 7B.

The results of subjecting the sensors and blanks to the foregoing conditions are summarized in the following table:

| Test condition | Microporous membrane stain | Nonporous polyethylene stain |
|---|---|---|
| Storage in phosphate buffered saline solution | Dark, even purple stain | Lighter color, less even |
| Storage in sensor housing assembly | Dark, even purple stain | Clear signs of abrasion, large voids in purple stain |
| Abrasion | Lighter purple stain, still evenly coated | Purple stain completely removed |
| Sonication with isopropanol | Lighter purple stain, still evenly coated | Purple stain completely removed |
| Control (no handling tests) | Dark, even purple stain | Dark, even purple stain |

These results demonstrate the superior durability of the benzalkonium heparin coating on the glucose sensor, having a porous polymeric surface and hydrophilic polymer matrix, as compared in benzalkonium heparin coating on a polymeric surface alone.

Example 4

Demonstration of Effectiveness of Antithrombotic Coating

12 GLUCATH® sensors with a benzalkonium/heparin coating and 12 BD L-Cath PICC lines (outside diameter 0.037 cm, 0.0145 inches; polyurethane) as controls without coating were prepared for insertion into the cardiovascular system of four sheep. The coated GluCath sensor was constructed of a fluorophore/quencher indicator system embedded in a hydrophilic acrylic matrix, as described in U.S. patent application Ser. No. 12/026,396. The benzalkonium heparin coating was applied as described in Example 3.

Sensors and control catheters were inserted into the left and right jugular veins and left and right cephalic veins, with the sensor on one side and the control catheter on the other of the same sheep. After 25 hours, two sheep were euthanized and the sensors and controls were surgically exposed and examined by incising and reflecting the skin and surrounding tissues overlying the test article and vein, and then opening the vein longitudinally taking care not to disturb the sensor or catheter or any cellular accumulation or debris on the test articles or in the veins. After 22 additional hours (47 hours elapsed time), two additional sheep were euthanized and the sensors surgically exposed and examined as described above.

Digital photographs of each sensor or catheter were taken in place. After examination, each sensor or catheter was removed from the vein, stained with methylene blue, and examined microscopically at 10-20× primary objective power to observe build up of fibrin or cellular material or surface irregularities the low the resolution of the photographs. Two of the test articles were found to have been placed outside of the vein, in the surrounding tissue, and were not included in the evaluations.

Tissue sections from the veins were also obtained and characterized for the state of the vessel in proximity to the test articles. The results of these evaluations are shown in the table below:

| Sensor/Article | Time (Hr) | Sheep | Vessel | Fibrin buildup on sensor (gross assessment) | Fibrin buildup on sensor (microscopic assessment) | Vessel Wall | Notes |
|---|---|---|---|---|---|---|---|
| 4-GluCath | 25 | 193/24 | LJS | 0 | 0 | NGHL | — |
| 5-GluCath | 25 | 193/24 | LJI | NA* | NA | NGHL | *Sensor not in vessel, tip of sensor kinked. |
| 6-GluCath | 25 | 193/24 | LC | 0 | 0 | Focal microscopic endothelial erosion, with minor fibrin deposition | Tip of sensor kinked. |
| 7-GluCath | 25 | 196/25 | RJS | 0 | 0 | NGHL | — |
| 8-GluCath | 25 | 196/25 | RJI | 0 | 1 (equivocal) | NGHL | — |
| 9-GluCath | 25 | 196/25 | RC | 0 | 0 | Focal microscopic endothelial erosion, with minor fibrin deposition | — |
| 1-BD-LC | 25 | 193/24 | RJS | 1 | 1 | NGHL | — |
| 2-BD-LC | 25 | 193/24 | RJI | 0** | 0 | NGHL | **Most of sensor inadvertently pulled from vessel during dissection. This may have stripped some surface deposits off the catheter surface. |
| 3-BD-LC | 25 | 193/24 | RC | 1 | 1 | NGHL | — |
| 10-BD-LC | 25 | 196/25 | LJS | 1 | 1 | NGHL | — |
| 11-BD-LC | 25 | 196/25 | LC | 1 | 1 | NGHL | — |
| 12-GluCath | 47 | 194/27 | RJS | 0 | 0 | NGHL | — |
| 13-GluCath | 47 | 194/27 | RJI | 0 | 0 | NGHL | Tip of sensor is elongated and kinked. |
| 14-GluCath | 47 | 194/27 | RC | 0 | 0 | Mass of fibrin on vessel wall at tip of sensor, endothelium intact. | Tip of sensor kinked. |
| 20-GluCath | 47 | 195/26 | LJS | 0 | 0 | NGHL | — |
| 21-GluCath | 47 | 195/26 | LJI | 0 | 0 | NGHL | — |
| 22-GluCath | 47 | 195/26 | LC | 0 | 0 | NGHL | — |
| 15-BD-LC | 47 | 194/27 | LJS | 1 | 1 | NGHL | — |
| 16-BD-LC | 47 | 194/27 | LJI | 0 | 1 | NGHL | — |
| 17-BD-LC | 47 | 194/27 | LC | 1 | 1 | NGHL | — |
| 18-BD-LC | 47 | 195/26 | RJS | 1 | 1 | NGHL | — |
| 19-BD-LC | 47 | 195/26 | RC | 0 | 0 | NGHL | — |

Note that in the foregoing table "RC" means "Right Cephalic," "LJS" means "Left Jugular Vein Superior," "LJI" means "Left Jugular Vein Inferior," "RJS" means "Right Jugular Vein Superior," "RJI" means "Right Jugular Vein Inferior," and "NGHL" means "no gross or histologic legions." Furthermore, the numeric descriptions contained in the foregoing table with respect to the gross and microscopic fibrin buildup on the sensors is a shorthand for the following:

"0" indicates none, or limited to hemostatic plug at venipuncture site only;

"1" indicates scant discontinuous or microscopic deposition only;

"2" indicates <1 mm in thickness;

"3" indicates >1 mm in thickness; and

"4" indicates complete vascular occlusion (thrombosis).

These evaluations demonstrate that the GluCath sensor with heparin/benzalkonium coating was superior to the control catheters in terms of fewer instances of macroscopic fibrin deposits and fewer instances of microscopic fibrin deposition.

Example 5

Sustained Release Heparin

Figure 8:
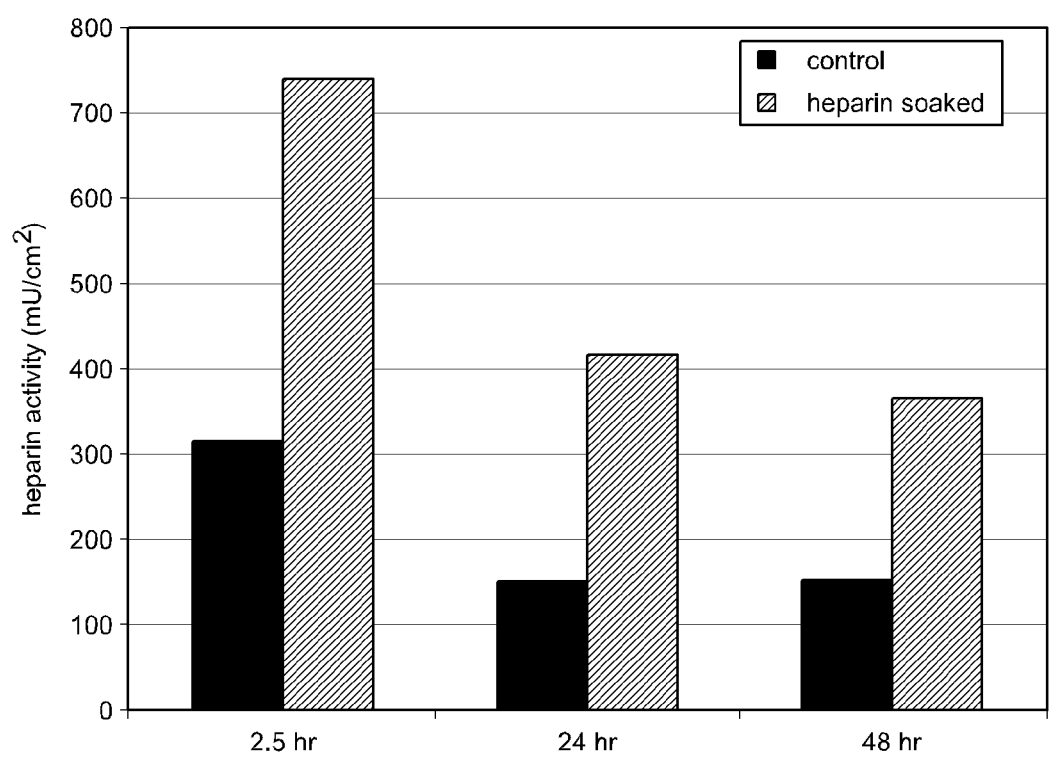
FIG. 8 shows the heparin activity of a glucose sensor that has undergone heparin soaking.

GluCath sensors were soaked in a 30% solution of sodium heparin in pH 5 phosphate buffered saline for two hours to saturate the hydrogel. After removal from the soak solution, the sensors were dip-coated with heparin benzalkonium in isopropyl alcohol to coat the outer surface. To serve as controls, other sensors which had not undergone the sodium heparin soaking step were also heparin benzalkonium dip-coated. After air drying overnight, the sensors were subjected to flowing buffer (pH 7.4 phosphate buffered saline at 37° C.) for up to 48 hours. At 2.5, 24, and 48 hours, the sensors were removed from the buffer and tested for heparin activity using a chromogenic anti-FXa activity assay. The results, shown in FIG. 8, showed that the heparin-soaked sensors retained higher levels of activity than the control sensors at each time point.

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An analyte sensor, comprising:
an elongate member;
an analyte-responsive indicator disposed along a distal portion of the elongate member, wherein said indicator is capable of generating a signal related to a concentration of analyte;
a porous membrane covering at least the indicator along the distal portion of the elongate member; and
a coating comprising heparin stably associated with at least a portion of the porous membrane, wherein the heparin is covalently bound to a chemical linking moiety comprising skeletal moiety selected from the group consisting of a $C_1$-$C_{10}$ alkyl group, a carbohydrate, a polyoxyethylene and a polypeptide, wherein the chemical linking moiety is covalently bound to the porous membrane.

2. The analyte sensor of claim 1, wherein the elongate member comprises an optical fiber comprising a light path.

3. The analyte sensor of claim 2, wherein the analyte-responsive indicator comprises a fluorophore operably coupled to an analyte binding moiety, wherein analyte binding causes a change in the emission intensity of the fluorophore, and wherein the analyte responsive indictor is disposed within the light path of the optical fiber.

4. The analyte sensor of claim 3, wherein the fluorophore is HPTS-triCysMA and the binding moiety is 3,3'-oBBV.

5. The analyte sensor of claim 1, wherein the analyte-responsive indicator is immobilized within a hydrogel that comprises heparin.

6. The analyte sensor of claim 1, wherein the porous membrane is a microporous membrane.

7. The analyte sensor of claim 6, wherein the microporous membrane comprises one or more polymers selected from a group consisting of the polyolefins, the fluoropolymers, the polycarbonates, and the polysulfones.

8. The analyte sensor of claim 6, wherein the microporous membrane comprises at least one fluoropolymer.

9. The analyte sensor of claim 8, wherein the at least one fluoropolymer is selected from the group consisting of polytetrafluoroethylene, perfluoroalkoxy polymer, fluorinated ethylene-propylene, polyethylenetetrafluoroethylene, polyvinylfluoride, polyethylenechlorotrifluoroethylene, polyvinylidene fluoride, polychlorotrifluoroethylene, perfluoropolyether, perfluoroelastomer, and fluoroelastomer.

10. The analyte sensor of claim 6, wherein the microporous membrane comprises at least one polyolefin.

11. The analyte sensor of claim 10, wherein the at least one polyolefin is polyethylene.

12. An analyte sensor, comprising:
an elongate member;
an analyte-responsive indicator disposed along a distal portion of the elongate member, wherein said indicator is capable of generating a signal related to a concentration of analyte;
a porous membrane covering at least the indicator along the distal portion of the elongate member; and
a coating comprising heparin stably associated with at least a portion of the porous membrane, wherein the heparin is covalently bound to a chemical linking moiety that is covalently bound to the porous membrane;
wherein a least the portion of the elongate member coated by the coating comprises high molecular weight polyamine.

13. The analyte sensor of claim 12, wherein the elongate member comprises an optical fiber comprising a light path.

14. The analyte sensor of claim 13, wherein the analyte-responsive indicator comprises a fluorophore operably coupled to an analyte binding moiety, wherein analyte binding causes a change in the emission intensity of the fluorophore, and wherein the analyte responsive indictor is disposed within the light path of the optical fiber.

15. The analyte sensor of claim 14, wherein the fluorophore is HPTS-triCysMA and the binding moiety is 3,3'-oBBV.

16. An analyte sensor, comprising:
an elongate member;
an analyte-responsive indicator disposed along a distal portion of the elongate member, wherein said indicator is capable of generating a signal related to a concentration of analyte;
a porous membrane covering at least the indicator along the distal portion of the elongate member; and
a coating comprising heparin stably associated with at least a portion of the porous membrane, wherein the heparin is covalently bound to a chemical linking moiety that is covalently bound to the porous membrane;
wherein the chemical linking moiety has the formula:
A-X—B; wherein A is a photochemically reactive group capable of covalently bonding to the porous membrane after activation by actinic radiation; B is a different reactive group from A and capable of covalently bonding to heparin; and X is a skeletal moiety that is resistant to cleavage in an aqueous physiological fluid and joins the A and B reactive groups.

17. The analyte sensor of claim 16, wherein the elongate member comprises an optical fiber comprising a light path.

18. The analyte sensor of claim 17, wherein the analyte-responsive indicator comprises a fluorophore operably coupled to an analyte binding moiety, wherein analyte binding causes a change in the emission intensity of the fluorophore, and wherein the analyte responsive indictor is disposed within the light path of the optical fiber.

19. The analyte sensor of claim 18, wherein the fluorophore is HPTS-triCysMA and the binding moiety is 3,3'-oBBV.

20. An analyte sensor, comprising:
an elongate member;
an analyte-responsive indicator disposed along a distal portion of the elongate member, wherein said indicator is capable of generating a signal related to a concentration of analyte;
a porous membrane covering at least the indicator along the distal portion of the elongate member; and
a coating comprising heparin stably associated with at least a portion of the porous membrane, wherein the heparin is covalently bound to a chemical linking moiety that is covalently bound to the porous membrane;
wherein the chemical linking moiety has the formula:

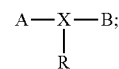

wherein A is a photochemically reactive group capable of covalently bonding to the porous membrane after activation by actinic radiation; B is a different reactive group from A and capable of covalently bonding to heparin; R is a selector group that is a member of a specific bonding pair; and X is a skeletal moiety that is resistant to cleavage in an aqueous physiological fluid and joins the A and B reactive groups.

21. The analyte sensor of claim 20, wherein the elongate member comprises an optical fiber comprising a light path.

22. The analyte sensor of claim 21, wherein the analyte-responsive indicator comprises a fluorophore operably coupled to an analyte binding moiety, wherein analyte binding causes a change in the emission intensity of the fluorophore, and wherein the analyte responsive indictor is disposed within the light path of the optical fiber.

23. The analyte sensor of claim 22, wherein the fluorophore is HPTS-triCysMA and the binding moiety is 3,3'-oBBV.

* * * * *